United States Patent [19]

Inamori et al.

[11] Patent Number: 4,925,864

[45] Date of Patent: May 15, 1990

[54] PHENYLTRIAZOLE DERIVATIVE AND INSECTICIDE

[75] Inventors: Masahito Inamori, Shizuoka; Tetsuo Horii, Fujieda; Tomonori Shimazu; Masaji Sugaya, both of Shizuoka, all of Japan

[73] Assignees: Kumiai Chemical Industry Co., Ltd.; Ihara Chemical Industry Co., Ltd., both of Tokyo, Japan

[21] Appl. No.: 171,777

[22] Filed: Mar. 22, 1988

[30] Foreign Application Priority Data

Mar. 27, 1987 [JP] Japan .................................. 62-73636
Nov. 11, 1987 [JP] Japan ............................... 62-284873

[51] Int. Cl.$^5$ ................. C07D 249/12; C07D 249/14; C07D 403/04; A01N 43/26
[52] U.S. Cl. .................................... 514/383; 514/384; 548/264.8; 548/265.4; 548/265.6; 548/264.2; 548/267.8; 548/268.6
[58] Field of Search ....................... 548/266, 265, 268; 514/383, 384

[56] References Cited

U.S. PATENT DOCUMENTS

| 3,489,761 | 1/1970 | Kauer . | |
|---|---|---|---|
| 4,038,405 | 7/1977 | Evans et al. . | |
| 4,414,221 | 11/1983 | Parsons et al. | 514/384 |
| 4,625,036 | 11/1986 | Boyle | 548/266 |

FOREIGN PATENT DOCUMENTS

| 0208321 | 7/1986 | European Pat. Off. . |
| 3129193 | 2/1983 | Fed. Rep. of Germany . |
| 2162590 | 7/1973 | France . |

Primary Examiner—Richard L. Raymond
Assistant Examiner—K. L. Konstas
Attorney, Agent, or Firm—Oblon, Spivak, McClelland, Maier & Neustadt

[57] ABSTRACT

A phenyltriazole derivative of the formula:

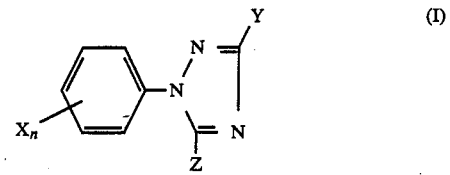

(I)

wherein X is a halogen atom, an alkyl group, a halogen-substituted alkyl group, an alkoxy group, a nitro group, a phenoxy group, an amino group, a cyano group, a 1-pyrrolyl group or a halogen-substituted alkoxy group, Y is a $C_2$–$C_6$ alkyl group which may be substituted by halogen, alkoxy, alkylthio, alkylsulfonyl, alkoxycarbonyl or carbamoyl, a methyl-substituted cycloalkyl group, an alkenyl group, a $C_1$–$C_4$ alkylsulfinyl group or a 2-methyl-1,3-dithiolan-2-yl group, Z is a hydrogen atom, a halogen atom, a halogen-substituted alkyl group, an alkoxyalkyl group, an alkenyloxyalkyl group, a methyl group, an alkylsulfinyl group, an alkylsulfonyl group, a phenyl group, a

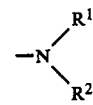

group, wherein each of $R^1$ and $R^2$ which may be the same or different is a hydrogen atom, an alkyl group, an alkoxy group, an acyl group, an amino group, a phenyl group, an alkenyl group, an alkynyl group, a dimethylcarbamoyl group, an alkoxycarbonyl group, a trichloromethylthio group or an alkylsulfonyl group which may be substituted by halogen, or $R^1$ and $R^2$ form together with the adjacent nitrogen atom, a hetero ring, or a

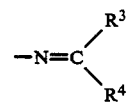

group wherein $R^3$ is a hydrogen atom of an alkylthio group and $R^4$ is an alkylthio group or an alkoxy group, and n is an integer of 0 to 5.

23 Claims, No Drawings

PHENYLTRIAZOLE DERIVATIVE AND INSECTICIDE

The present invention relates to a 1-phenyltriazole derivative and an insecticide containing it as the active ingredient.

U.S. Pat. Nos. 4,038,405 and 4,097,599 disclose that triazole derivatives having a phenyl group at the 1-position and a trifluoromethyl group at the 3-position can be used as active ingredients of insecticides or miticides. Further, Belgian Patents 824,737 and 828,162 disclose that triazole compounds having a phenyl group at the 1-position and an organic phosphate residue at the 3-position are effective as inseticides, miticides and nematocides. Furthermore, European Patent Application EP 208321-A discloses that triazole derivatives having a substituted or unsubstitued phenyl group at the 1-position and a substituted or unsubstituted phenyl group at the 3-position are effective as insecticides or miticides.

However, the insecticidal activities of these compounds are not necessarily adequate.

The present inventors have synthesized various 1-phenyltriazole derivatives and conducted extensive studies on their physiological activities with an aim to develop a useful insecticide. As a result, it has been found that the compounds of the present invention have excellent insecticidal activities against various noxious insects, particularly against brown rice planthopper (*Nilaparvata lugens* Stal). The present invention is based on this discovery.

The present invention provides a phenyltriazole derivative of the formula:

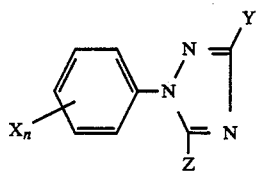

(I)

wherein X is a halogen atom, an alkyl group, preferably a $C_1$–$C_6$ alkyl group, a halogen-substituted alkyl group, preferably a halogen-substituted $C_1$–$C_4$ alkyl group, an alkoxy group, preferably a $C_1$–$C_4$ alkoxy group, a nitro group, a phenoxy group, an amino group, a cyano group, a 1-pyrrolyl group or a halogen-substituted alkoxy group, preferably a halogen-substituted $C_1$–$C_4$ alkoxy group, Y is a $C_2$–$C_6$ alkyl group which may be substituted by halogen, alkoxy, preferably $C_1$–$C_4$ alkoxy, alkylthio, preferably $C_1$–$C_4$ alkylthio, alkylsulfonyl, preferably $C_1$–$C_4$ alkylsulfonyl, alkoxycarbonyl, preferably $C_1$–$C_4$ alkoxycarbonyl or carbamoyl, a methyl-substituted cycloalkyl group, an alkenyl group, preferably a $C_3$–$C_5$ alkenyl group, a $C_1$–$C_4$ alkylsulfinyl group, preferably a methylsulfinyl group, or a 2-methyl-1,3-dithiolan-2-yl group, Z is a hydrogen atom, a halogen atom, a halogen-substituted alkyl group, preferably a halogen-substituted $C_1$–$C_4$ alkyl group, an alkoxyalkyl group, preferably a $C_1$–$C_4$ alkoxy-$C_1$–$C_4$ alkyl group, an alkenyloxyalkyl group, preferably $C_3$–$C_5$ alkenyloxy-$C_1$–$C_4$ alkyl group, a methyl group, an alkylsulfinyl group, preferably a $C_1$–$C_4$ alkylsulfinyl group, an alkylsulfonyl group, preferably $C_1$–$C_4$ alkylsulfonyl group, a phenyl group, a

group, wherein each of $R^1$ and $R^2$ which may be the same or different is a hydrogen atom, an alkyl group, preferably a $C_1$–$C_6$ alkyl group, an alkoxy group, preferably a $C_1$–$C_4$ alkoxy group, an acyl group, preferably a $C_1$–$C_4$ acyl group, an amino group, a phenyl group, an alkenyl group, preferably $C_3$–$C_5$ alkenyl group, an alkynyl group, preferably $C_3$–$C_5$ alkynyl group, a dimethylcarbamoyl group, an alkoxycarbonyl group, preferably a $C_1$–$C_4$ alkoxycarbonyl group, a trichloromethylthio group or an alkylsulfonyl group, preferably a $C_1$–$C_4$ alkylsulfonyl group which may be substituted by halogen, or $R^1$ and $R^2$ form together with the adjacent nitrogen atom, a hetero ring, or a

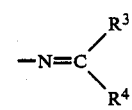

group wherein $R^3$ is a hydrogen atom or an alkylthio group, preferably a $C_1$–$C_4$ alkylthio group and $R^4$ is an alkylthio group, preferably a $C_1$–$C_4$ alkylthio group or an alkoxy group, preferably a $C_1$–$C_4$ alkoxy group, and n is an integer of 0 to 5.

Now, present invention will be described in detail with reference to the preferred embodiments.

Among the phenyltriazole derivatives of the formula I, preferred compounds are represented by the formula:

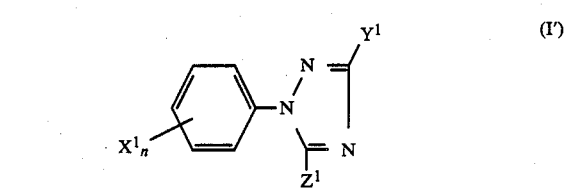

(I')

wherein $X^1$ is a halogen atom, a trifluoromethyl group, a trifluoromethoxy group, a nitro group or a 1-pyrrolyl group, $Y^1$ is a $C_2$–$C_6$ alkyl group which may be substituted by halogen, a methylsulfinyl group or a

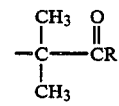

group wherein R is an alkoxy group or an amino group, $Z^1$ is a hydrogen atom, a halogen atom, an methyl group, an alkoxyalkyl group, a phenyl group, an alkoxymethylideneamino group, a 1-pyrrolyl group or a

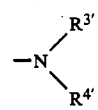

group wherein each of $R^{3'}$ and $R^{4'}$ which may be the same or different is a hydrogen atom, an acyl group, an alkenyl group, an alkynyl group, an alkyl group, an alkoxy group, a trichloromethylthio group, a dimethylcarbamoyl group, a methanesulfonyl group which may be substituted by chlorine or an alkoxycarbonyl group, and n is 2 or 3.

More preferred are compounds represented by the formula:

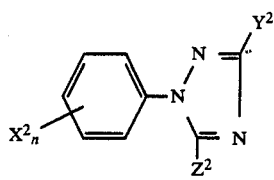

(I″)

wherein $X^2$ is a halogen atom, a trifluoromethyl group, a trifluoromethoxy group or a nitro group, $Y^2$ is a $C_2$–$C_4$ alkyl group which may be substituted by halogen, a methylsulfinyl group, or a 1-methyl-1-carbamoylethyl group, $Z^2$ is a hydrogen atom, a halogen atom, a methyl group, a phenyl group, an alkoxy methylideneamino group, a 1-pyrrolyl group or a

group wherein each of $R^5$ and $R^6$ which may be the same or different is a hydrogen atom, an alkyl group, an alkynyl group, an alkoxy group, an acyl group, an alkenyl group, an alkoxycarbonyl group or a trichloromethylthio group, and n is an ingeter of from 0 to 5.

Particularly preferred are compounds represented by the formula:

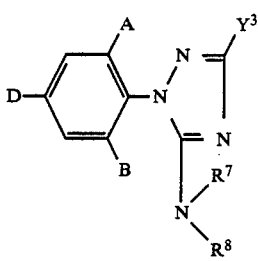

(I‴)

wherein each of A and B which may be the same or different is a chlorine atom or a nitro group, D is a trifluoromethyl group or a trifluoromethoxy group, $Y^3$ is a $C_2$–$C_4$ alkyl group which may be substituted by halogen, and each of $R^7$ and $R^8$ which may be the same or different is a hydrogen atom, an acyl group, an alkenyl group, an alkynyl group or an alkyl group.

More specifically, compounds presented by the following formulas are most preferred:

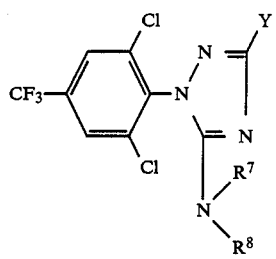

(i)

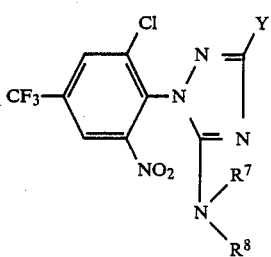

(ii)

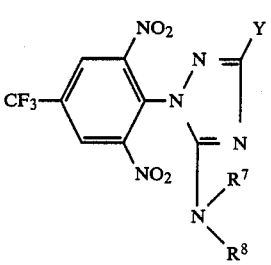

(iii)

or

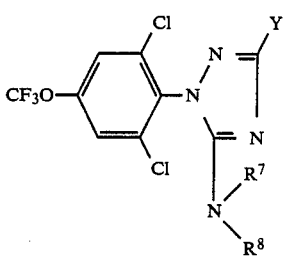

(iv)

wherein Y, $R^7$ and $R^8$ are as defined above. Particularly preferred are the compounds wherein Y is a tertiary butyl or a $C_2$–$C_4$ alkyl group which is substituted by halogen, and each of $R^7$ and $R^8$ which may be the same or different is a hydrogen atom, a methyl group, an ethyl group or a propyl group.

Specific examples of the compound of the present invention will be presented in Table 1. Compound Nos. identified in the Table will be referred to in the following description.

TABLE 1

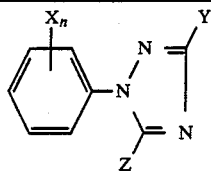

| Compound No. | $X_n$ | Y | Z | Melting point (°C.) or refractive index($n_D^{20}$) |
|---|---|---|---|---|
| 1 | 2-Cl | tert-$C_4H_9$ | $CH_3$ | 95–97 |
| 2 | 3-Cl | " | " | 1.5442 |
| 3 | 4-Cl | " | " | 129–131 |
| 4 | 2,4-$Cl_2$ | " | " | 99–100 |
| 5 | 2,6-$Cl_2$ | " | " | 66–70 |
| 6 | 2,4-$Br_2$ | " | " | 106–107 |
| 7 | 2,4-$F_2$ | " | " | 64–66 |
| 8 | 2,4,6-$Cl_3$ | " | " | 128.5–130.5 |
| 9 | 2,4,6-$Br_3$ | " | " | 138–139 |
| 10 | 2,4-$F_2$,3,5-$Cl_2$ | " | " | 76–78 |
| 11 | 3-$CF_3$ | " | " | 1.4833 |
| 12 | 4-Cl,3-$CF_3$ | " | " | 75–77 |
| 13 | 4-Cl,2-$CF_3$ | " | " | 53–56 |
| 14 | 2-Cl,5-$CF_3$ | tert-$C_4H_9$ | $CH_3$ | 1.4928 |
| 15 | H | " | " | 1.5327 |
| 16 | 4-$CH_3$ | " | " | Not measurable |
| 17 | 2-Br,4-$C_4H_9$ | " | " | 1.5289 |
| 18 | 2-$OCH_3$ | " | " | 1.5295 |
| 19 | 2,4,6-$Cl_3$ | iso-$C_3H_7$ | " | 102–106 |
| 20 | " | " | Cl | 108–112 |
| 21 | " | tert-$C_4H_9$ | H | 52–55 |
| 22 | 3-Cl | " | Cl | 1.5486 |
| 23 | 4-Br | " | " | 1.5678 |
| 24 | 2,4-$Cl_2$ | " | " | 69–70 |
| 25 | 2,6-$Cl_2$ | " | " | 90–92 |
| 26 | 2,4-$Br_2$ | " | " | 76–78 |
| 27 | 3-Cl,4-F | " | " | 1.5341 |
| 28 | 2,4,6-$Cl_3$ | tert-$C_4H_9$ | Cl | 98–98.5 |
| 29 | 2,4,6-$Br_3$ | " | " | 119–121 |
| 30 | 2,4-$F_2$,3,5-$Cl_2$ | " | " | 1.5305 |
| 31 | 2,3,4,5,6-$F_5$ | " | " | 1.4690 |
| 32 | 3-$CF_3$ | " | " | 1.4983 |
| 33 | 4-Cl,2-$CF_3$ | " | " | 57–58 |
| 34 | 2,4,6-$Cl_3$ | " | Br | 101–103 |
| 35 | 2-$CF_3$ | " | $N(C_2H_5)_2$ | 1.4850 |
| 36 | 3-$CF_3$ | " | " | 1.4977 |
| 37 | 2,4-$Cl_2$ | " | " | 1.5321 |
| 38 | 2-F,4-Cl | " | " | 1.5241 |
| 39 | 2,4-$F_2$ | " | " | Not measurable |
| 40 | 2-Cl,4,6-$F_2$ | " | " | 1.5085 |
| 41 | 2,4-$Cl_2$,6-F | " | " | 1.5270 |
| 42 | 2-Cl,5-$CF_3$ | tert-$C_4H_9$ | $N(C_2H_5)_2$ | 1.4950 |
| 43 | 4-Cl,2-$CF_3$ | " | " | 1.4949 |
| 44 | 2,4-$Cl_2$,6-$CF_3$ | " | " | 1.5070 |
| 45 | 2-$NO_2$,4-$CF_3$ | " | " | 1.4911 |
| 46 | 4-$NO_2$,2-$CF_3$ | " | " | 1.5141 |
| 47 | 2,3-$Cl_2$ | " | " | 1.5322 |
| 48 | 2,6-$Cl_2$ | " | " | 1.5293 |
| 49 | 2,6-$F_2$ | " | " | 65–69 |
| 50 | 2,4,6-$F_3$ | " | " | 49–51 |
| 51 | 2,4,6-$Cl_3$ | $C_2F_5$ | " | 66–70 |
| 52 | " | iso-$C_3H_7$ | " | 86.5–87.5 |
| 53 | " | tert-$C_4H_9$ | " | 1.5290 |
| 54 | " | $C(CH_3)_2C_3H_7$ | " | 1.5381 |
| 55 | " | ▽—$CH_3$ | " | 1.5661 |
| 56 | 2,4,6-$Cl_3$ | $C(CH_3)_2SCH_3$ | $N(C_2H_5)_2$ | 63–64 |
| 57 | " | $C(CH_3)_2CH_2Cl$ | " | 1.5527 |
| 58 | 2,4-$Cl_2$,6-F | $C_2F_5$ | " | Not measurable |
| 59 | 2,4-$Cl_2$,6-$CF_3$ | " | " | 64–72 |
| 60 | 2,4,6-$Cl_3$ | $C_3F_7$ | " | 1.4877 |
| 61 | " | tert-$C_4H_9$ | $NH_2$ | 211–214 |
| 62 | " | " | $NHCH_3$ | 165–166 |
| 63 | " | " | $NHC_2H_5$ | 73–74 |
| 64 | " | " | $N(CH_3)_2$ | 68–71 |
| 65 | " | " | $N(C_3H_7)_2$ | 1.5332 |

TABLE 1-continued

[Structure: phenyl ring with $X_n$ substituents, connected to N-N=C(Y) and N=C(Z) groups]

| Compound No. | $X_n$ | Y | Z | Melting point (°C.) or refractive index($n_D^{20}$) |
|---|---|---|---|---|
| 66 | " | " | $N(C_3H_7\text{-iso})_2$ | 106–108 |
| 67 | " | " | $N(C_2H_5)C_3H_7$ | 1.5293 |
| 68 | " | " | $N(CH_3)OCH_3$ | 1.5490 |
| 69 | " | " | $N(CH_3)COCH_3$ | 93–94 |
| 70 | 2,4,6-$Cl_3$ | tert-$C_4H_9$ | $NHCOCH_3$ | 134–136 |
| 71 | " | $C(CH_3)=CH_2$ | $N(C_3H_7)_2$ | 144–145 |
| 72 | " | tert-$C_4H_9$ | $CH_2Cl$ | 88–90 |
| 73 | " | " | $CH_2OCH_3$ | 53–54 |
| 74 | 3-$CF_3$ | " | " | 1.4871 |
| 75 | 2,4,6-$Cl_3$ | " | $CH_2OCH_2CH=CH_2$ | 34–37 |
| 76 | " | " | $SO_2CH_3$ | 179–180 |
| 77 | 4-O-phenyl | " | $N(C_2H_5)_2$ | Not measurable |
| 78 | " | " | $CH_3$ | 1.5574 |
| 79 | 2,3,4-$F_3$ | " | $N(C_2H_5)_2$ | 1.4939 |
| 80 | 2,6-$Cl_2$,4-$CF_3$ | " | " | 1.5012 |
| 81 | 2-Cl,F-4 | " | " | 1.5180 |
| 82 | 2,3,4-$Cl_3$ | " | " | 1.5470 |
| 83 | 2-Cl,4-$CF_3$ | " | " | 1.4951 |
| 84 | 2-$NO_2$,4-$CF_3$ | tert-$C_4H_9$ | $NH_2$ | 173–176 |
| 85 | 2,4-$Cl_2$ | $C_2F_5$ | $N(C_2H_5)_2$ | 1.4999 |
| 86 | 2,4-$Cl_2$,3-CN | tert-$C_4H_9$ | " | 1.5503 |
| 87 | 2,6-$(NO_2)_2$,4-$CF_3$ | " | " | 64–65 |
| 88 | 2,5-$Cl_2$,3-$CF_3$ | " | " | 1.5039 |
| 89 | 2,6-$Cl_2$,4-F | " | " | 1.5211 |
| 90 | 2,6-$Cl_2$,4-$CF_3$ | " | $NH_2$ | 208–212 |
| 91 | 2,6-$Cl_2$,4-$CF_3$ | " | $CH_3$ | 95–97 |
| 92 | 2,4-$Cl_2$,3-$CH_3$ | " | $N(C_2H_5)_2$ | 1.5439 |
| 93 | 2,6-$Cl_2$,4-$CF_3$ | " | H | 88–92 |
| 94 | " | " | Cl | 69–70 |
| 95 | " | " | $N(C_3H_7)_2$ | 1.4940 |
| 96 | 2-Cl,4-$CF_3$,6-$NO_2$ | " | $N(C_2H_5)_2$ | 1.4992 |
| 97 | 2,4-$Br_2$ | tert-$C_4H_9$ | $N(C_2H_5)_2$ | 1.5603 |
| 98 | 2,6-$Cl_2$,4-$CF_3$ | $C_2F_5$ | " | 1.4672 |
| 99 | 2,6-$(NO_2)_2$,4-$CF_3$ | tert-$C_4H_9$ | $NH_2$ | 236–239 |
| 100 | 2,4,6-$Cl_3$ | $C_2F_5$ | " | 150–158 |
| 101 | " | " | H | 1.4950 |
| 102 | 2,6-$(NO_2)_2$,4-$CF_3$ | tert-$C_4H_9$ | " | 1.5010 |
| 103 | 2-$CF_3$,4,5-$Cl_2$ | " | $N(C_2H_5)_2$ | 1.5037 |
| 104 | 2,6-$Cl_2$,4-$CF_3$ | $CH(CH_3)CF_3$ | " | 1.4809 |
| 105 | " | $C_2F_5$ | H | 1.4530 |
| 106 | 2-$NO_2$,4-$CF_3$ | tert-$C_4H_9$ | Cl | 85–89 |
| 107 | " | $C_2F_5$ | H | 1.4601 |
| 108 | 2,6-$Cl_2$,4-$CF_3$ | $C_3F_7$ | $N(C_2H_5)_2$ | 1.4550 |
| 109 | 2,6-$(NO_2)_2$,4-$CF_3$ | tert-$C_4H_9$ | $CH_3$ | 1.5054 |
| 110 | 2-$NO_2$,4-$CF_3$ | tert-$C_4H_9$ | $CH_3$ | 84–102 |
| 111 | 2,4,6-$Cl_3$ | $C(CH_3)_2OCH_3$ | $N(C_2H_5)_2$ | 1.5449 |
| 112 | 2-$NO_2$,4-$CF_3$ | $C_2F_5$ | " | 1.4678 |
| 113 | 2-Cl,4-$OCF_3$ | tert-$C_4H_9$ | " | 1.4879 |
| 114 | 2,6-$Cl_2$,4-$CF_3$ | $C(CH_3)_2CH_2Cl$ | " | 1.5061 |
| 115 | 2,4,6-$Cl_3$ | $CH(CH_3)CF_3$ | $N(C_2H_5)_2$ | Not measurable |
| 116 | 2,6-$Cl_2$,4-$CF_3$ | $C(CH_3)_2CH_2Cl$ | $NH_2$ | 169–171 |
| 117 | " | tert-$C_4H_9$ | $N(COCH_3)_2$ | 1.5028 |
| 118 | " | " | $NHCOCH_3$ | 174–176 |
| 119 | " | " | $NHC_2H_5$ | 1.5083 |
| 120 | " | $CH(CH_3)CF_3$ | $NH_2$ | 205–209 |
| 121 | 2,6-$Cl_2$,4-$CF_3$ | $CH(CH_3)CF_3$ | H | 1.4752 |
| 122 | 2-Cl,4-$CF_3$,6-$NO_2$ | tert-$C_4H_9$ | $NH_2$ | 133–135.5 |
| 123 | 2,6-$Cl_2$,4-$CF_3$ | tert-$C_4H_9$ | NHCOH | 133–139 |
| 124 | 2-Cl,4-$CF_3$,6-$NO_2$ | " | H | 56–58 |
| 125 | " | " | $CH_3$ | 76–79 |
| 126 | 2-$NO_2$,4-$CF_3$ | " | H | 69–71 |
| 127 | 2,6-$Cl_2$,4-$CF_3$ | $C_2F_5$ | $NH_2$ | 181–183 |
| 128 | 2-Cl,4-$CF_3$ | tert-$C_4H_9$ | " | 174–175 |

TABLE 1-continued

[Structure: phenyl with $X_n$ substituents, connected via N-N to a ring system with Y and Z substituents]

| Compound No. | $X_n$ | Y | Z | Melting point (°C.) or refractive index($n_D^{20}$) |
|---|---|---|---|---|
| 129 | 2-Cl,4-OCF$_3$ | " | " | 159–161 |
| 130 | 2,4-Cl$_2$,6-CF$_3$ | " | " | 177–179 |
| 131 | 2,4-Cl$_2$,6-F | " | " | 196–199 |
| 132 | 2-Cl,4-CF$_3$,6-F | " | N(C$_2$H$_5$)$_2$ | 1.4853 |
| 133 | 3,5-(CF$_3$)$_2$ | " | NH$_2$ | 161–163 |
| 134 | 2,4,6-F$_3$ | " | " | 217–220 |
| 135 | 2,6-Cl$_2$,4-CF$_3$ | " | NHC$_3$H$_7$ | 1.4981 |
| 136 | 2,6-Cl$_2$,4-CF$_3$ | tert-C$_4$H$_9$ | NHC$_3$H$_7$-iso | 103–110 |
| 137 | " | iso-C$_3$H$_7$ | NH$_2$ | 183–185 |
| 138 | " | tert-C$_4$H$_9$ | NHCH$_3$ | 153–158 |
| 139 | 2,4-Cl$_2$ | " | CH$_2$Cl | 1.5486 |
| 140 | 2,4,6-Cl$_3$ | " | N=C(SCH$_3$)$_2$ | 166–168 |
| 141 | " | " | N=C(SCH$_3$)—OC$_2$H$_5$ | 116–117 |
| 142 | " | " | N(CH$_3$)—C$_6$H$_5$ | 147–154 |
| 143 | " | " | —N(pyrrolidinyl) | 1.5684 |
| 144 | 2,6-Cl$_2$,4-CF$_3$ | " | " | 37–40 |
| 145 | " | " | N=C(SCH$_3$)$_2$ | 163–166 |
| 146 | " | " | NHCO$_2$C$_2$H$_5$ | 130–135 |
| 147 | 2-Cl,4-CF$_3$,6-NH$_2$ | " | N(C$_2$H$_5$)$_2$ | 155–157 |
| 148 | 2-Cl,4-CF$_3$,6-N(pyrrolidinyl) | " | " | 1.5202 |
| 149 | 2,4-Cl$_2$,6-F | tert-C$_4$H$_9$ | —N(pyrrolidinyl) | 76–78 |
| 150 | 2,4-Cl$_2$,6-CF$_3$ | " | " | 1.5363 |
| 151 | 2,6-Cl$_2$,4-OCF$_3$ | " | NH$_2$ | 207–211 |
| 152 | 3-CF$_3$ | " | " | 120–122 |
| 153 | 4-CF$_3$ | " | " | 167–170 |
| 154 | 2,6-Cl$_2$,4-OCF$_3$ | " | N(C$_2$H$_5$)$_2$ | 1.4940 |
| 155 | " | " | —N(pyrrolidinyl) | 1.5221 |
| 156 | 2,6-Cl$_2$,4-CF$_3$ | " | NHCH$_2$C≡CH | 1.5142 |
| 157 | " | " | N(CH$_2$C≡CH)$_2$ | 109–112 |
| 158 | 2-Cl,4-CF$_3$,6-I | " | N(C$_2$H$_5$)$_2$ | 60–63 |
| 159 | 2,6-Cl$_2$,4-CF$_3$ | " | N(CH$_2$CH=CH$_2$)$_2$ | 1.5059 |
| 160 | " | " | NHCH$_2$CH=CH$_2$ | 1.5060 |
| 161 | " | C$_2$H$_5$ | NH$_2$ | 172–174 |
| 162 | 2,6-Cl$_2$,4-CF$_3$ | tert-C$_4$H$_9$ | N(CH$_3$)OCH$_3$ | 1.4965 |
| 163 | 2,4,6-F$_3$ | " | —N(pyrrolidinyl) | 87–88 |

TABLE 1-continued

| Compound No. | $X_n$ | Y | Z | Melting point (°C.) or refractive index($n_D^{20}$) |
|---|---|---|---|---|
| 164 | 2,6-Cl$_2$,4-CF$_3$ | " | N(CH$_3$)$_2$ | 82–84 |
| 165 | " | " | N(C$_3$H$_7$-iso)$_2$ | 80–83 |
| 166 | 2-Cl,4-CF$_3$ | C$_2$F$_5$ | H | 77–85 |
| 167 | " | " | N(C$_2$H$_5$)$_2$ | 1.4609 |
| 168 | 2,4-Cl$_2$ | " | H | 34–38 |
| 169 | " | " | CH$_3$ | 1.4855 |
| 170 | " | tert-C$_4$H$_9$ | NH$_2$ | 188–191 |
| 171 | 2,6-Cl$_2$,4-CF$_3$ | " | S(O)CH$_3$ | 130–137 |
| 172 | " | C(CF$_3$)$_2$CH$_3$ | NH$_2$ | 224–225.5 |
| 173 | " | " | N(C$_2$H$_5$)$_2$ | 1.4699 |
| 174 | " | C(CH$_3$)$_2$—COOC$_2$H$_5$ | " | 1.4950 |
| 175 | 2,6-Cl$_2$,4-CF$_3$ | S(O)CH$_3$ | NH$_2$ | 253–257 |
| 176 | " | sec-C$_4$H$_9$ | " | 188–189 |
| 177 | " | tert-C$_4$H$_9$ | NHCON(CH$_3$)$_2$ | 113–118 |
| 178 | " | " | NHCOC$_2$H$_5$ | 151–153 |
| 179 | " | " | N(CH$_3$)COCH$_3$ | 77–80 |
| 180 | " | " | NHCOC$_3$H$_7$ | 140–143 |
| 181 | 2,4-F$_2$,6-Cl | " | NH$_2$ | 224–230 |
| 182 | " | " | —N⟨pyrrolyl⟩ | 61–63 |
| 183 | 2,6-Cl$_2$,4-CF$_3$ | C(CH$_3$)$_2$—CONH$_2$ | NH$_2$ | 265–270 |
| 184 | " | tert-C$_4$H$_9$ | N(CH$_3$)SCCl$_3$ | 1.5271 |
| 185 | " | " | N(C$_2$H$_5$)—SCCl$_3$ | 1.5229 |
| 186 | " | " | N(C$_2$H$_5$)OCCH$_3$ | 1.4971 |
| 187 | " | " | N=CHOC$_2$H$_5$ | 1.5070 |
| 188 | 2,6-Cl$_2$,4-CF$_3$ | tert-C$_4$H$_9$ | NHSO$_2$CH$_2$Cl | 159–161 |
| 189 | " | " | NHSO$_2$CH$_3$ | 188–191 |
| 190 | " | " | Br | 1.5141 |
| 191 | 2,3,4-F$_3$ | " | NH$_2$ | 197–199 |
| 192 | 2-F,4-Cl | " | " | 171–174 |
| 193 | 2,5-Cl$_2$ | C$_2$F$_5$ | N(C$_2$H$_5$)$_2$ | 38–43 |
| 194 | 2,6-Cl$_2$,4-CF$_3$ | tert-C$_4$H$_9$ | —C$_6$H$_5$ (phenyl) | 1.5232 |
| 195 | 2,3,4-F$_3$ | " | —N⟨pyrrolyl⟩ | 85–87 |
| 196 | 2,6-Cl$_2$,4-CF$_3$ | C(CH$_3$)$_2$—SC$_3$H$_7$ | NH$_2$ | 156–157.5 |
| 197 | " | C(CH$_3$)$_2$—SC$_2$H$_5$ | " | 188–190 |
| 198 | " | C(CH$_3$)$_2$—SC$_3$H$_7$ | N(C$_2$H$_5$)$_2$ | 1.5172 |
| 199 | " | tert-C$_4$H$_9$ | NHNH$_2$ | 154–159 |
| 200 | " | " | —N—N=⟨pyrazolyl⟩ | 1.5200 |
| 201 | 2,6-Cl$_2$,4-CF$_3$ | C(CH$_3$)$_2$—SO$_2$C$_3$H$_7$ | NH$_2$ | 261–266 |
| 202 | " | C(CH$_3$)$_2$—SO$_2$C$_2$H$_5$ | " | 248–252 |
| 203 | " | C(CH$_3$)(S-)(S-) dithietane with CH$_3$ | " | 213–215 |

TABLE 1-continued

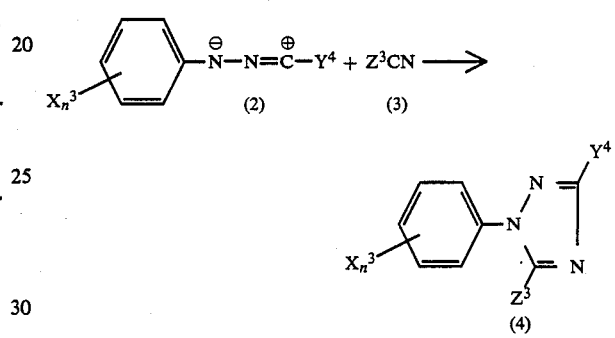

| Compound No. | $X_n$ | Y | Z | Melting point (°C.) or refractive index($n_D^{20}$) |
|---|---|---|---|---|
| 204 | " | $C(CH_3)_2-SO_2C_3H_7$ | $N(C_2H_5)_2$ | 111.5–112.5 |
| 205 | " | tert-$C_4H_9$ | $N=CHOCH_3$ | 1.5081 |

NMR values of the compounds of the present invention are shown in Table 1-1.

TABLE 1-1

| Compound No. | Substituent NMR: δ (CDCl$_3$) | Benzene ring NMR: δ (CDCl$_3$) |
|---|---|---|
| 16 | 1.42s(Me × 3) 2.40s(Me) 2.45s(Me) | 7.30s(4H) |
| 39 | 1.00t(Me × 2) 1.40s(Me × 3) 3.17q(CH$_2$ × 2) | 6.83–7.67m(3H) |
| 58 | 1.06t(Me × 2) 3.17q(CH$_2$ × 2) | 7.26dd(1H) 7.41d(1H) |
| 77 | 1.03t(Me × 2) 1.37s(Me × 3) 2.13q(CH$_2$ × 2) | 6.93–7.60m(9H) |

Particularly preferred specific compounds are as follows:

5-Amino-1-(2,6-dichloro-4-trifluoromethylphenyl)-3-(1,1-dimethylethyl)-1H-1,2,4-triazole, 1-(2,6-dichloro-4-trifluoromethylphenyl)-3-(1,1-dimethylethyl)-5-(N-ethylamino)-1H-1,2,4-triazole, 1-(2,6-dichloro-4-trifluoromethylphenyl)-3-(1,1-dimethylethyl)-5-(N-propylamino)-1H-1,2,4-triazole, 1-(2,6-dichloro-4-trifluoromethylphenyl)-5-(N,N-diethylamino)-3-(1-trifluoromethylethyl)-1H-1,2,4-triazole, 5-amino-1-(2,6-dichloro-4-trifluoromethylphenyl)-3-pentafluoroethyl-1H-1,2,4-triazole, 5-(N,N-diethylamino)-3-(1,1-dimethylethyl)-1-(2,6-dinitro-4-trifluoromethylphenyl)-1H-1,2,4-triazole, 1-(2-chloro-6-nitro-4-trifluoromethylphenyl)-5-(N,N-diethylamino)-3-(1,1-dimethylethyl)-1H-1,2,4-triazole, and 1-(2,6-dichloro-4-trifluoromethoxyphenyl)-5-(N,N-diethylamino)-3-(1,1-dimethylethyl-1H-1,2,4-triazole.

The compounds of the present invention can be prepared in accordance with the following Reaction schemes.

Reaction scheme 1

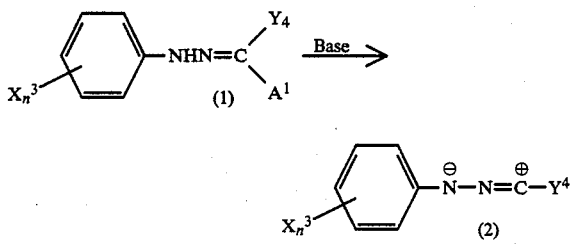

-continued
Reaction scheme 1

In the above formulas, $X^3$ is a halogen atom, an alkyl group, a halogen-substituted alkyl group, a nitro group, a halogen-substituted alkoxy group, an alkoxy group, a phenoxy group or a cyano group, n is an integer of from 0 to 5, $A^1$ is a halogen atom, $Y^4$ is a $C_2$-$C_6$ alkyl group which may be substituted by halogen, alkoxy or alkylthio, an alkenyl group, a methyl-substituted cycloalkyl group or a $$-\overset{CH_3}{\underset{CH_3}{C}}-COR_9$$

wherein $R^9$ is an alkoxy group, and $Z^3$ is a methyl group, a halogen-substituted alkyl group, an akoxyalkyl group, a phenyl group or a $$-N\overset{R^{10}}{\underset{R^{11}}{\diagdown}}$$

group wherein each of $R^{10}$ and $R^{11}$ which may be the same or different is a hydrogen atom, an alkyl group, an alkoxy group or a phenyl group which may be substituted by halogen or methyl.

In this reaction, a hydrazidoyl halide of the formula (1) is reacted with a base to form a nitrile imine intermediate of the formula (2).

The base to be used here includes tertiary amines such as trialkylamines, N,N-dialkylanilines and aromatic amines. Such as base is used in an amount of from 1 to 3 molar times.

The formed nitrile imine intermediate may be subjected, without being isolated, to the 1,3-cyclo addition reaction with a nitrile of the formula (3), whereby the desired compound of the formula (4) can be produced.

This reaction may be conducted in a suitable inert solvent or without using any solvent. The solvent may be an aromatic hydrocarbon such as benzene, toluene or xylene, an halogenized aromatic hydrocarbon compound such as chlorobenzene or dichlorobenzene, an halogenized aliphatic hydrocarbon compound such as carbon tetrachloride, chloroform or dichloromethane, or an ether such as diethyl ether or tetrahydrofuran. In a case where the nitrile of the formula (3) is liquid, an excess amount of the nitrile may be used as the solvent.

The reaction temperature and the reaction time vary depending upon the reactivity of the starting materials and can not generally be defined. However, in a case where the hydrazidoyl halide of the formula (1) is hydrazidoyl bromide, the reaction adequately proceeds at a temperature of from 10° to 80° C. for from 0.5 to 1 hour. Likewise, in the case of hydrazidoyl chloride, the desired compound can be produced in good yield by conducting the reaction within a temperature range of from 10° C. to the boiling point of the solvent used, preferably from room temperature to 100° C. for from 1 to 10 hours.

In the case of 1-phenyltriazole derivatives i.e. the compounds of the present invention where the 5-position is a hydrogen atom, such compounds can be produced in accordance with the following Reaction scheme.

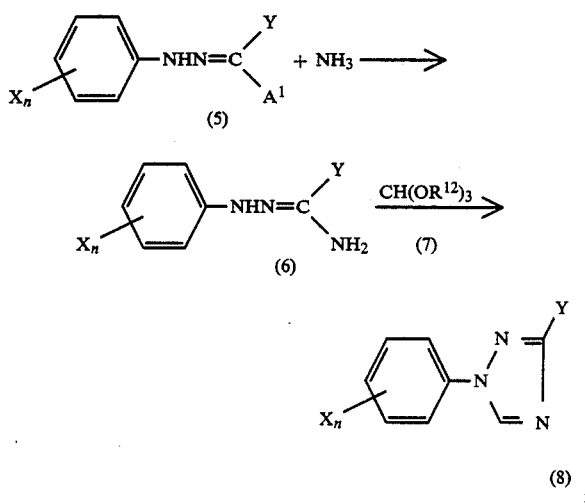

In the above formulas, X, Y, $A^1$ and n are as defined above, and $R^{12}$ is a lower alkyl group.

In this process, firstly, a hydrazidoyl halide of the formula (5) and ammonia are reacted in water or in an inert solvent to obtain a compound of the formula (6). Then, the compound of the formula (6) thus obtained is reacted with an ortho formate of the formula (7) to obtain the desired compound of the formula (8). The ortho formate is used in an amount of at least the stoichiometric amount, and it may be used also as the solvent.

The reaction temperature may optionally be selected within a temperature range from room temperature to the boiling point of the solvent to be used. The reaction time varies depending upon the reactivity of the starting materials and can not generally be defined. However, it is usually possible to obtain the desired compound in good yield by the reaction for from 2 to 10 hours. Further, by using an organic acid such as formic acid as a catalyst, it is possible to obtain the desired compound more efficiently.

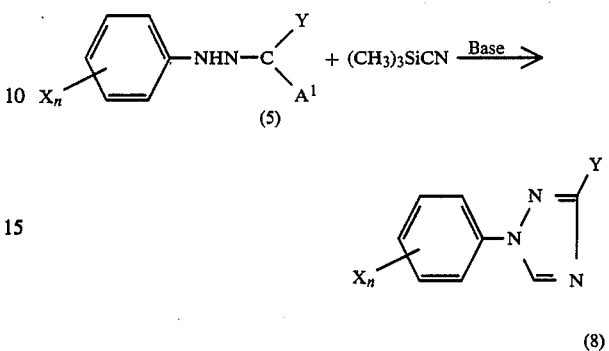

In the above formulas, X, Y, $A^1$ and n are as defined above.

In accordance with this Reaction scheme, a compound of the formula (8) can be prepared by reacting the hydrazidoyl halide of the formula (5) with a nitrile as shown above.

Further, in the case where the 5-position is a phenyl group which may be substituted, such a compound may be prepared by a process represented by the Reaction scheme 2'.

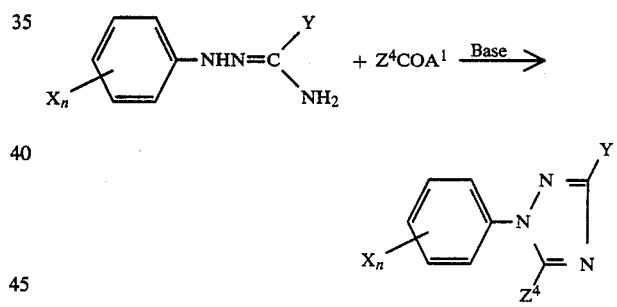

In the above formulas, X, Y, A and n are as defined above, and $Z^4$ is a phenyl group which may be substituted.

The reaction may be conducted in the presence of a tertiary organic base, and the reaction temperature may optionally be selected within a temperature range of from room temperature to the boiling point of the solvent to be used.

The desired product can be produced in good yield, for example, by refluxing for from 0.5 to 1 hour in an excess amount of pyridine which serves also as the solvent.

As shown in the Reaction scheme 3, the compound wherein the 5-position is a halogen atom can be prepared by firstly synthesizing a compound of the formula (10) wherein the 5-position is a hydroxyl group or a triazolone compound of the formula (11) as its tautomer, and then further halogenating such a compound with a phosphorus oxyhalide of the formula (12) or with a phenyl phosphoric acid dihalide of the formula (13).

Reaction scheme 3

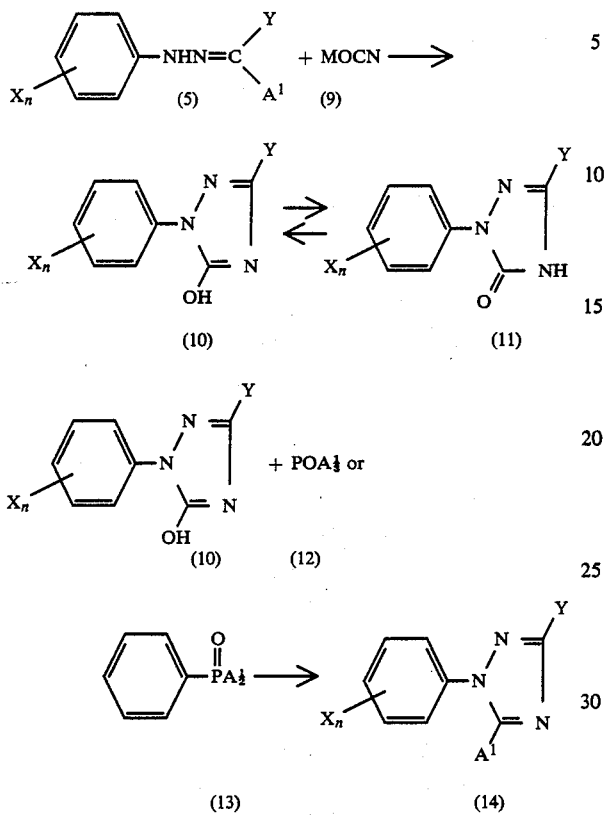

In the above formulas, X, Y, A¹ and n are as defined above, and M is an alkali metal atom.

Here, the compound of the formula (14) can be prepared in good yield by conducting the reaction at the boiling point of the solvent for from 2 to 24 hours when the phosphorus oxyhalide of the formula (12) is used, or by conducting the reaction at a temperature of from 150° acid 180° C. for 1 to 2 hours when the phenylphosphonic acid dihalide of the formula (13) is used.

A compound wherein the 5-position is an alkylsulfonyl group can be prepared by a process shown in the Reaction scheme 4.

Reaction scheme 4

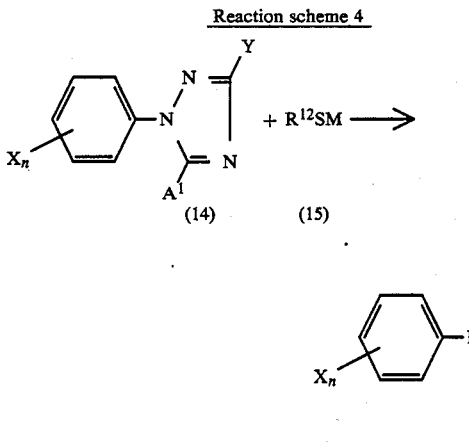

-continued
Reaction scheme 4

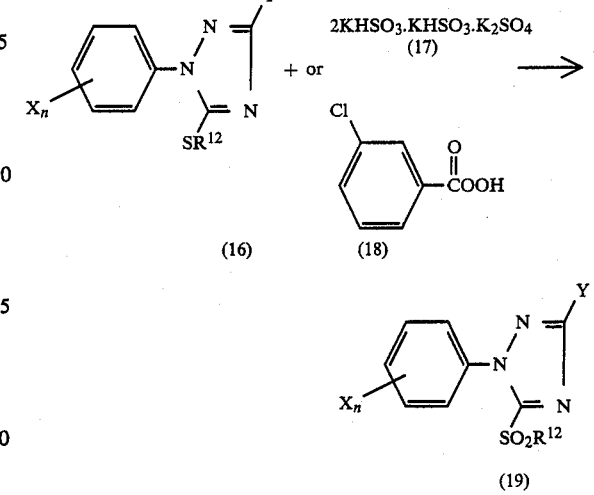

In the above formulas, X, Y, A¹, R¹² and n are as defined above.

Namely, firstly an alkylthio derivative of the formula (16) is prepared, and it is then oxidized by a suitable oxidizing agent such as Oxone ® (trade mark, E. I. Du Pont, U.S.A.) of the formula (17) or a m-chloroperpenzoic acid of the formula (18). In this case, the oxidizing agent may be used in an excess amount.

Further, a compound wherein the 5-position is an alkylsulfinyl group can be prepared as an intermediate for the preparation of an alkylsulfonyl compound by using the above oxidizing agent in an equivalent amount as shown in the Reaction scheme 5.

Reaction scheme 5

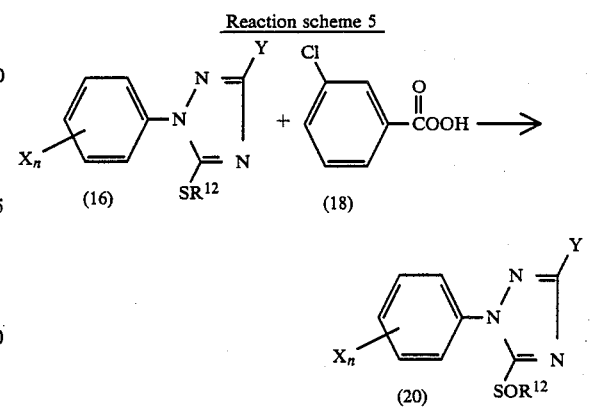

In the above formulas, X, Y, R¹² and n are as defined above.

A compound wherein the 5-position is an alkenyloxyalkyl group can be prepared in accordance with the Reaction scheme 6.

Reaction scheme 6

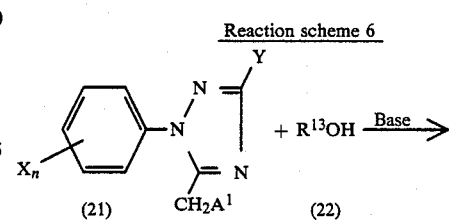

-continued
Reaction scheme 6

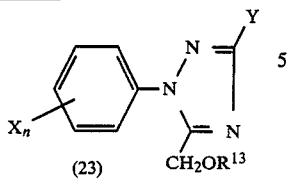
(23)

Reaction scheme 8

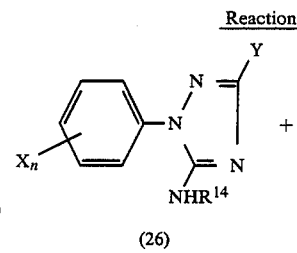
(26)

In the above formulas, $R^{13}$ is an alkenyl group, and X, Y, $A^1$ and n are as defined above.

Namely, a haloalkyl derivative of the formula (21) prepared by the process of the Reaction scheme 1 and an alkenyl alcohol of the formula (22) are reacted in the presence of a base such as an alkali metal hydride.

Further, a compound wherein the 5-position is an alkoxy methylidene amino group can be prepared by a process represented by the Reaction scheme 7.

Reaction scheme 7

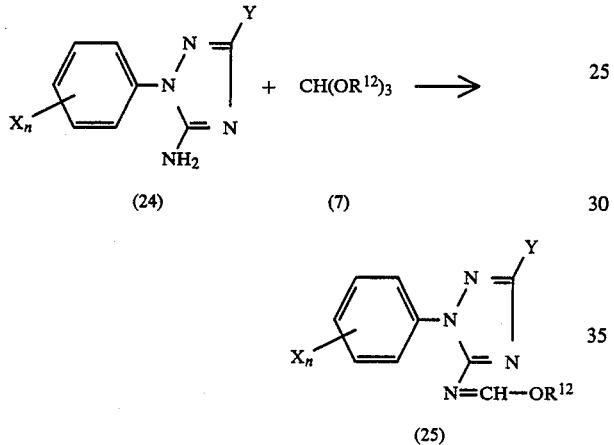

In the above formulas, X, Y, $R^{12}$ and n are as defined above.

Namely, the compound of the formula (25) can be prepared by reacting a 5-amino derivative of the formula (24) prepared by the Reaction scheme 1 with an orthoformate of the formula (7).

A compound wherein the 5-position is a

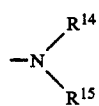

group or a

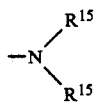

group wherein $R^{14}$ is a hydrogen atom or an alkyl group, and $R^{15}$ is an acyl group, an alkenyl group, an alkynyl group, an alkyl group, a dimethylcarbamoyl group, an alkoxycarbonyl group, a trichloromethylthio group or an alkylsulfonyl group which may be substituted by halogen, can be prepared by a process represented by the Reaction scheme 8.

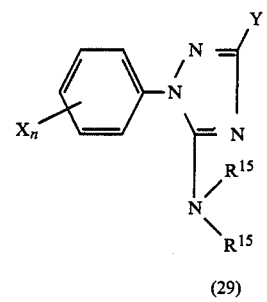

In the above formulas, X, Y, $R^{14}$, $R^{15}$, $A^1$ and n are as defined above.

Namely, the desired compound of the formula (28) or (29) can be prepared by reacting a 5-amino derivative of the formula (26) prepared by the Reaction scheme 1 with a halogen compound of the formula (27) in the presence of a base. The base may be an inorganic base or a tertiary amine such as a trialkyl amine, an N,N-dialkylaniline or an aromatic amine, or an alcoholate, and it may be used at least an equimolar amount. Particularly when it is a liquid, it may be used in an excess amount as serving as a solvent. The reaction may be conducted in a suitable inert solvent. The solvent may be, for example, an aromatic hydrocarbon such as benzene, toluene or xylene, an aliphatic halogen compound such as carbon tetrachloride, chloroform or dichloromethane, or an ether such as diethyl ether, tetrahydrofuran or dioxane.

The reaction time and the reaction temperature vary depending upon the compound and can not generally be determined. Further, when $R^{15}$ is an acetyl group, the desired product can be obtained by a reaction with an acid anhydride. When $R^{15}$ is a formyl group, the desired product can be prepared by heating with formic acid. A compound wherein the 5-position is a hetero ring may be prepared, for example, by the Reaction scheme 9.

Reaction scheme 9

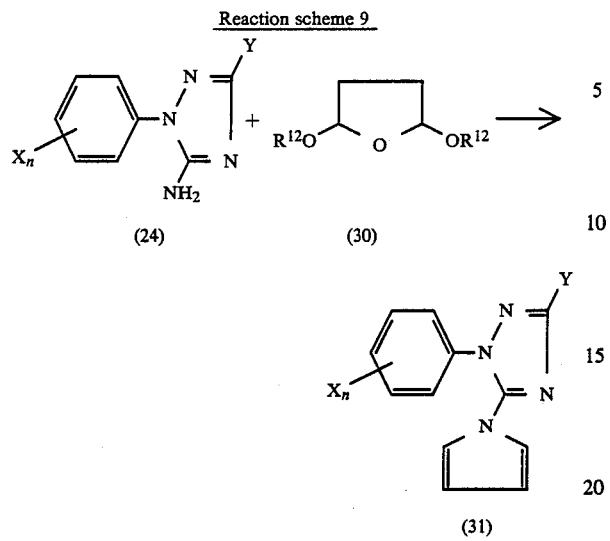

Reaction scheme 10

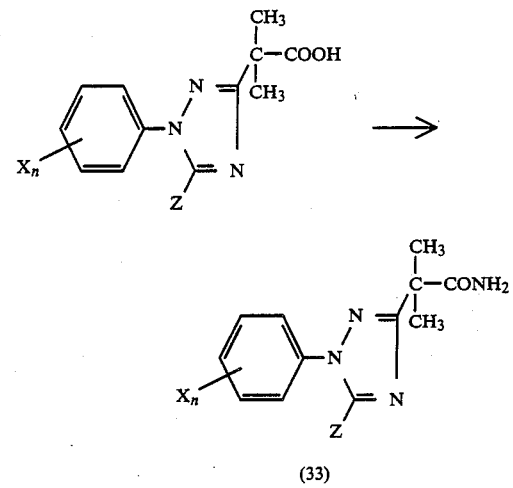

Namely, a 5-pyrrolyl compound of the formula (31) can be prepared by reacting a 5-amino derivative of the formula (24) prepared in accordance with the Reaction scheme 1, with a tetrahydrofuran derivative of the formula (30). The reaction may be conducted in an inert solvent at a temperature of from room temperature to 120° C. for from 0.5 to 2 hours under stirring, whereby the desired product can be prepared in good yield.

Further, a compound wherein X is an amino group can be prepared by reducing a nitro compound prepared in accordance with the Reaction scheme 1, by a suitable conventional method. Further, a derivative wherein X is a pyrrolyl group can be prepared by reacting this aniline derivative with a tetrahydrofuran derivative of the formula (30). A compound wherein X is a fluorine atom can be prepared by reacting a chlorine-substituted compound or a nitro-substituted compound prepared in accordance with the Reaction scheme 1 with a potassium fluoride. In this case, the reaction will be advantageous particularly when the benzene ring is substituted by an electron attractive group such as a nitro group or a trifluoromethyl group, in addition to the chlorine atom or nitro group.

Further, a compound wherein Y is a

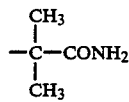

group can be prepared from an ester of the formula (32) prepared in accordance with the Reaction scheme 1, as shown by the Reaction scheme 10.

Reaction scheme 10

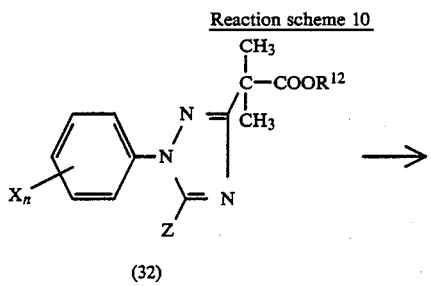

in the above formulas, X, Z, n and $R^{12}$ are as defined above.

Namely, the desired amide compound of the formula (33) can be prepared by hydrolyzing an ester compound of the formula (32) by a conventional method by means of e.g. a base and reacting it with N,N'-carbonyldiimidazole and then with ammonia.

Now, the processes for the production of the compounds of the present invention will be described with reference to Examples. However, it should be understood that the present invention is by no means restricted by such specific Examples.

EXAMPLE 1

Preparation of 5-amino-3-(tert-butyl)-1-(2,6-dichloro-4-trifluoromethylphenyl)-1H-1,2,4-triazole 7.0 g (0.02 mol) of 2,2-dimethylpropionyl chloride 2,6-dichloro-4-trifluoromethylphenylhydrazone and 1.7 g (0.04 mol) of cyanamide were added to 100 ml of tetrahydrofuran. Then, 4.0 g (0.04 mol) of triethylamine was dropwise added under reflux and stirring. After completion of the dropwise addition, the stirring was continued at the same temperature for further 1 hour. After cooling, the reaction solution was poured into water, and the precipitate was extracted with toluene. The organic layer was washed with water and dried. Then, the solvent was distilled off under reduced pressure, and the residue was washed with n-hexane to obtain 5.3 g (yield: 74.6%) of the desired compound as white prismatic crystals. The melting point: 208°–212° C.

EXAMPLE 2

Preparation of 1-(2-nitro-4-trifluoromethylphenyl)-3-(pentafluoroethyl)-1H-1,2,4-triazole 11.0 g (0.03 mol) of pentafluoropropionylamide 2-nitro-4-trifluoromethylhydrazone and 14.8 g (0.01 mol) of ethyl orthoformate were mixed and refluxed for 10 hours. The reaction mixture was cooled, and excess ethyl orthoformate was distilled off under reduced pressure. The residue was purified by silica gel column chromatography to obtain 13.8 g (yield: 61.1%) of the

EXAMPLE 3

Preparation of
(5-(N,N-diethylamino)-3-(1-methoxy-isopropyl)-1-(2,4,6-trichlorophenyl)-1H-1,2,4-triazole 6.6 g (0.02 mol) of 1-methoxy-iso-butyryl chloride 2,4,6-trichlorophenylhydrazone and 2.0 g (0.02 mol) of N,N-diethylcyanamide were added to 100 ml of toluene. Then, 2.2 g (0.02 mol) of triethylamine was dropwise added under stirring at room temperature. After completion of the dropwise addition, stirring was continued at room temperature for further 1 hour. To the reaction solution, 100 ml of toluene was added. Then, the organic layer was washed with water and dried. Then, the solvent was distilled off under reduced pressure, and the residue was purified by silica gel column chromatography to obtain 7 g (yield: 89.7%) of the desired compound as a pale yellow liquid. Refractive index $n_D^{20}$: 1.5449.

EXAMPLE 4

Preparation of
5-(N,N-diethylamino)-3-(tert-butyl)-1-(2-nitro-4-trifluoromethylphenyl)-1H-1,2,4-triazole 7.4 g (0.02 mol) of 2,2-dimethylpropionyl bromide 2-nitro-4-trifluoromethylphenylhydrazone and 2.0 g (0.02 mol) of N,N-diethylcyanamide were added to 100 ml of toluene. Then, 2.2 g (0.022 mol) of triethylamine was dropwise added under stirring at room temperature. After completion of the dropwise addition, stirring was continued at room temperature for further 1 hour. Then, 100 ml of toluene was added and washed with water. The organic layer was dried, and the solvent was distilled off. The residue was purified by silica gel column chromatography to obtain 6.5 g (yield: 84.4%) of the desired compound as a pale yellow liquid. Refractive index $n_D^{20}$: 1.4911.

EXAMPLE 5

Preparation of
5-(N,N-diethylamino)-3-(pentafluoroethyl)-1-(2,4,6-trichlorophenyl)-1H-1,2,4-triazole 3.4 g (0.008 mol) of pentafluoropropionyl bromide 2,4,6-trichlorophenylhydrazone and 0.8 g (0.008 mol) of N,N-diethylcyanamide were added to 20 ml of toluene. Then, 0.9 g (0.009 mol) of triethylamine was added thereto under stirring at room temperature. After completion of the dropwise addition, stirring was continued at room temperature for further 1 hour. Then, 20 ml of toluene was added thereto, followed by washing with water. The organic layer was dried, and the solvent was distilled off. The residue was purified by silica gel column chromatography to obtain 1.9 g (yield: 54.3%) of the desired compound as a brown powder. Melting point: 66°-70° C.

EXAMPLE 6

Preparation of
5-chloro-3-(tert-butyl)-1-(2,4,6-trichlorophenyl)-1H-1,2,4-triazole 6.3 g (0.02 mol) of 2,2-dimethylpropionyl chloride 2,4,6-trichlorophenylhydrazone was dissolved in 50 ml of ethanol. Then, a solution of 3.2 g (0.04 mol) of potassium cyanate in 30 ml of water, was dropwise added thereto under stirring at room temperature. After completion of the dropwise addition, stirring was continued at the same temperature for further 0.5 hour. The precipitated crystals were collected by filtration and washed with n-hexane to obtain 6.1 g (yield: 95.3%) of 5-hydroxy-3-(tert-butyl)-1-(2,4,6-trichlorophenyl)-1H-1,2,4-triazole as white powder having a melting point of from 272° to 274° C.

4.8 g (0.015 mol) of 5-hydroxy-3-(tert-butyl)-1-(2,4,6-trichlorophenyl)-1H-1,2,4-triazole was added to 20 ml of phosphorus oxychloride, and stirred under reflux for 24 hours. The reaction mixture was cooled, and excess phosphorus oxychloride was distilled off under reduced pressure. To the residue, 100 ml of dichloromethane was added, and the mixture was washed with water. Then, the dichloromethane layer was dried, and the solvent was distilled off. The residue thereby obtained was purified by silica gel column chromatography to obtain 4.3 g (yield: 84.3%) of the desired compound as white needle like crystals. Melting point 98°-98.5° C.

EXAMPLE 7

Preparation of
3-(tert-butyl)-5-methylsulfonyl-1-(2,4,6-trichlorophenyl)-1H-1,2,4-triazole 3.5 g (0.01 mol) of 3-(tert-butyl)-5-methylthio-1-(2,4,6-trichlorophenyl)-1H-1,2,4-triazole was added to 120 ml of 85% ethanol, and 24.6 g (0.04 mol) of Oxone (trade mark) was further added thereto. The mixture was stirred at room temperature for 4 hours. Then, water was added to such an extent that Oxone (as described above) remained in a small amount, and the mixture was extracted with dichloromethane. The dichloromethane layer was dried, and then the solvent was distilled off. The residue was purified by silica gel column chromatography to obtain 3.0 g (yield: 78.9 g) of the desired compound as white powder. Melting point: 179°-180° C.

EXAMPLE 8

Preparation of
5-(N-acetyl-N-methylamino)-3-(tert-butyl)-1-(2,4,6-trichlorophenyl)-1H-1,2,4-triazole 3.6 g (0.01 mol) of 2,2-dimethylpropionyl bromide 2,4,6-trichlorophenylhydrazone and 0.6 g (0.01 mol) of N-methylcyanamide were added to 50 ml of toluene. Then, 1.1 g (0.011 mol) of triethylamine was dropwise added under stirring at room temperature. After the dropwise addition, stirring was continued at the same temperature for further 1 hour. After washing the reaction mixture with water, the toluene layer was dried, and the solvent was distilled off. The residue was purified by silica gel column chromatography to obtain 2.8 g (yield: 85%) of 3-(tert-butyl)-5-(N-methylamino)-1-(2,4,6-trichlorophenyl)-1H-1,2,4-triazole as power having a melting point of from 165° to 166° C.

6.7 g (0.02 mol) of 3-(tert-butyl)-5-(N-methylamino)-1-(2,4,6-trichlorophenyl)-1H-1,2,4-triazole was added to 51 g (0.5 mol) of acetic anhydride, and the mixture was stirred under reflux for 1 hour. Then, excess acetic anhydride was distilled off under reduced pressure. The residue was purified by silica gel column chromatography to obtain 5.5 g (yield: 73.3 g) of the desired compound as white powder. Melting point: 93°-94° C.

EXAMPLE 9

Preparation of
3-(tert-butyl)-5-(2-propenyloxymethyl)-1-(2,4,6-trichlorophenyl)-1H-1,2,4-triazole 17.9 g (0.05 mol) of 2,2-dimethylpropionyl bromide 2,4,6-trichlorophenylhydrazone and 3.8 g (0.05 mol) of chloroacetonitrile were added to 100 ml of toluene. Then, 5.6 g (0.055 mol) of triethylamine was dropwise added thereto under cooling with ice and stirring. After completion of the dropwise addition, stirring was continued at the same temperature for 30 minutes and then at room temperature for 1 hour. Then, 100 ml of toluene was added thereto, and the mixture was washed with water. The organic layer was dried, and the solvent was distilled off. The residue was purified by silica gel column chromatography to obtain 13.6 g (yield: 76.8%) of 5-chloromethyl-2-(tert-butyl)-1-(2,4,6-trichlorophenyl)-1H-1,2,4-triazole as pale yellow prismatic crystals having a melting point of from 88° to 90° C.

To 20 ml of allyl alcohol, 0.4 g (0.008 mol) of 50% sodium hydride was added, and the mixture was stirred at room temperature for 30 minutes. Then, 2.8 g (0.008 mol) of 5-chloromethyl-3-(tert-butyl)-1-(2,4,6-trichlorophenyl)-1H-1,2,4-triazole was gradually added thereto under stirring at room temperature. After completion of the dropwise addition, the solution was heated and stirred under reflux for 2 hours. Then, 50 ml of ethyl acetate was added thereto, and the mixture was washed with water. The organic layer was dried, and the solvent was distilled off. The oily substance thereby obtained was purified by silica gel column chromatography to obtain 1.8 g (yield: 60.0%) of the desired compound as pale yellow prismatic crystals. Melting point: 34°–37° C.

EXAMPLE 10

Preparation of
5-amino-1-(2,6-dichloro-4-trifluoromethylphenyl)-3-pentafluoroethyl-1H-1,2,4-triazole 20.5 g (0.05 mol) of pentafluoropropionyl chloride 2,6-dichloro-4-trifluoromethylphenylhydrazone and 2.5 g (0.06 mol) of cyanamide were added to 50 ml of tetrahydrofuran, and 6.1 g (0.06 mol) of triethylamine was dropwise added thereto under reflux and stirring. After completion of the dropwise addition, the mixture was stirred at the same temperature for 1 hour to complete the reaction. After cooling, the reaction solution was poured into water, and the precipitate was extracted with ethyl acetate. The organic layer was washed with water and dried. Then, the solvent was distilled off under reduced pressure, and the residue was washed with n-hexane to obtain 12.5 g (yield: 60.1%) of the desired compound as white powder. Melting point: 181°–183° C.

EXAMPLE 11

Preparation of
1-(2,6-dichloro-4-trifluoromethoxyphenyl)-5-(N,N-diethylamino)-3-(tert-butyl)-1H-1,2,4-triazole 7.3 g (0.02 mol) of 2,2-dimethylpropionyl chloride 2,6-dichloro-4-trifluoromethoxyphenylhydrazone and 2.0 g (0.02 mol) of N,N-diethylcyanamide were added to 100 ml of tetrahydrofuran, and 2.2 g (0.02 mol) of triethylamine was dropwise added under reflux and stirring. After completion of the dropwise addition, the mixture was stirred at the same temperature for 0.5 hour. After cooling, the reaction solution was poured into water, and the precipitate was extracted with chloroform. The chloroform layer was washed with water and dried, and the solvent was distilled off under reduced pressure. The residue was purified by silica gel column chromatography to obtain 7.4 g (yield: 87.1%) of the desired compound as a pale yellow liquid. Refractive index $n_D^{20}$: 1.4940.

EXAMPLE 12

Preparation of
1-(2,6-dichloro-4-trifluoromethylphenyl)-3-(tert-butyl)-5-(N-ethylamino)-1H-1,2,4-triazole In the same manner as in Example 1 except that the cyanamide was changed to N-ethylcyanamide, 3.9 g (yield: 51.3%) of the desired compound was obtained as pale yellow powder. Melting point: 67°–70° C.

EXAMPLE 13

Preparation of
1-(2,6-dichloro-4-trifluoromethylphenyl)-3-(tert-butyl)-5-(N-propylamino)-1H-1,2,4-triazole In the same manner as in Example 1 except that the cyanamide was changed to N-propylcyanamide and purification was conducted by silica gel column chromatography, 5.9 g (yield: 74.7%) of the desired compound was obtained as a colorless liquid. Refractive index $n_D^{20}$: 1.4981.

EXAMPLE 14

Preparation of
1-(2,6-dichloro-4-trifluoromethylphenyl)-5-(N,N-diethylamino)-3-(1-trifluoromethylethyl)-1H-1,2,4-triazole In the same manner as in Example 3 except that the 1-methoxy-iso-butyryl chloride 2,4,6-trichlorophenylhydrazone was changed to 2-trifluoromethylpropionyl chloride 2,6-dichloro-4-trifluoromethylphenylhydrazone, 5.0 g (yield: 55.6%) of the desired compound was obtained as a pale yellow liquid. Refractive index $n_D^{20}$: 1.4809.

EXAMPLE 15

Preparation of
5-(N,N-diethylamino)-3-(tert-butyl)-1-(2,6-dinitro-4-trifluoromethylphenyl)-1H-1,2,4-triazole In the same manner as in Example 11 except that 2,2-dimethylpropionyl chloride 2,6-dichloro-4-trifluoromethoxyphenylhydrazone was changed to 2,2-dimethylpropionyl chloride 2,6-dinitro-4-trifluoromethylphenylhydrazone, 5.1 g (yield: 59.3%) of the desired compound was obtained was obtained as yellow powder. Melting point: 64°–65° C.

EXAMPLE 16

Preparation of
1-(2-chloro-6-nitro-4-trifluoromethylphenyl)-5-(N,N-diethylamino)-3-(tert-butyl)-1H-1,2,4-triazole In the same manner as in Example 11 except that the 2,2-dimethylpropionyl chloride 2,6-dichloro-4-trifluoromethoxyphenylhydrazone was changed to 2,2-dimethylpropionyl chloride 2-chloro-6-nitro-4-trifluoromethylphenylhydrazone, 6.1 g (yield: 72.6%) of the desired compound was obtained as a yellow liquid. Refractive index $n_D^{20}$: 1.4992.

As intermediates, useful for the preparation of the compounds of the present invention, the compounds as shown in Table 2 may be mentioned. However, the intermediates are not limited to such specific Examples.

TABLE 2

X—⟨benzene ring⟩—NHMH$_2$

| Intermediate No. | X | Melting point (°C.) |
| --- | --- | --- |
| 1 | 2,4-Cl$_2$,6-F | 106.5–107.5 |
| 2 | 2,6-Cl$_2$,4-F | 117–119 |
| 3 | 2,6-Cl,4,6-F$_2$ | 90–91 |
| 4 | 2,3,4-F$_3$ | 88–88.5 |
| 5 | 2,5-Cl$_2$,3-CF$_3$ | 101–102 |
| 6 | 4,5-Cl$_2$,2-CF$_3$ | 84–85 |
| 7 | 2-Cl,4-F | |
| 8 | 2,6-F$_2$ | |
| 9 | 2,4-F$_2$,3,5-Cl$_2$ | |

NMR(CDCl$_3$): δ

| Intermediate No. | Benzene ring | NH | NH$_2$ |
| --- | --- | --- | --- |
| 7 | 6.73–7.56(m,3H) | 5.30–6.10 | 3.10–4.20 |
| 8 | 6.70–7.10(m,3H) | 5.80–4.30 | 3.40–4.50 |

Now, the preparation of intermediates will be described with reference to a Preparation Example of an intermediate.

PREPARATION OF 2,6-DICHLORO-4-FLUOROPHENYLHYDRAZINE (INTERMEDIATE NO. 2)

9.0 g (0.05 mol) of 2,6-dichloro-4-fluoroaniline was added to 50 ml of concentrated hydrochloric acid, and a solution of 3.8 g (0.055 mol) of sodium nitrite in 25 ml of water was dropwise added thereto at a temperature of from 0° to 5° C. After completion of the dropwise addition, the mixture was stirred at the same temperature for further 1 hour. Insolubles were removed by filtration, and the filtrate was dropwise added at a temperature of from 0° to 10° C. to a solution of 33.8 g (0.15 mol) of stannous chloride dihydrate in 50 ml of concentrated hydrochloric acid. After completion of the dropwise addition, the mixture was stirred at the same temperature for further 2 hours. The precipitated hydrochloride was collected by filtration, and 50 ml of water was added thereto. The mixture was made alkaline with an addition of 20% sodium hydroxide, and the precipitated solid was extracted with ethyl ether. The ethyl ether layer was washed with water and dried over anhydrous sodium sulfate. Then, the solvent was distilled off. The residue thereby obtained was washed with cold n-hexane to obtain 6.9 g (yield: 70.4%) of the desired compound as white feather-like crystals. Melting point: 117°–119° C.

The insecticide of the present invention comprises an insecticidally effective amount of the above described phenyltriazole derivative and an agricultural carrier. The phenyltriazole derivative of the present invention can be used by itself as an insecticide. However, it is common to formulate it into a usual insecticidal formulation. Namely, it is common to formulate it into an insecticidal formuation such as an emulsifiable concentrate, wettable powder, a dust or a granule by combining it with various adjuvants such as diluents, solvents, and surfactants.

The diluents include clay, talc, bentonite, diatomaceous earth and silica powder. The solvents include cyclohexanone, xylene, toluene, methyl ethyl ketone, isopropyl alcohol, methylnaphthalene and dimethylnaphthalene. Surfactants include metal salts of an alkylbenzene sulfonic acid, polyoxyethylenealkylaryl ethers, sodium alkylsulfate, metal salts of dinaphthylmethane disulfonic acid, metal salts of an alkylnaphthalene sulfonic acid and metal salts of lignin sulfonic acid.

The proportion of the active ingredient is suitably selected as the case requires. In the case of a dust or a granule, the proportion of the active ingredient is usually from 0.1 to 20% by weight, and in the case of an emulsifiable concentrate or wettable powder, it is usually from 5 to 80% by weight.

The insecticide of the present invention may be used for foliage application, soil treatment, treatment on the nursely box, etc.

The dose of the insecticide of the present invention varies depending upon the type of the compound used, the insect to be killed, the degree of outbreak, the degree of damage, the environmental conditions, the types of formulation to be used, etc. In the case of a dust or a granule which is applied by itself, the dose of an active ingredient is suitably selected within a range of from 0.1 g to 5 kg, preferably from 1 g to 1 kg, per 10 are. In the case of an emulsifiable concentrate or a wettable powder which is eventually used in the form of a liquid, the concentration may suitably be selected within a range of from 0.1 to 10,000 ppm, preferably from 10 to 3,000 ppm.

Now, Formulation Examples of the insecticide of the present invention will be given. However, it should be understood that the types and the proportions of the compounds and the adjuvants are not restricted by these specific Examples, and may be varied within wide ranges. In the following Examples, "parts" means "parts by weight".

FORMULATION EXAMPLE 1

Emulsifiable concentrate

30 Parts of Compound No. 1, 20 parts of cyclohexanone, 11 parts of polyoxyethylenealkylaryl ether, 4 parts of calcium alkylbenzenesulfonate and 35 parts of methylnaphthalene were uniformly dispersed to obtain an emulsifiable concentrate.

FORMULATION EXAMPLE 2

Wettable powder

40 Parts of Compound No. 14, 15 parts of diatomaceous earth, 15 parts of clay, 25 parts of silica powder, 2 parts of sodium dinaphthylmethane disulfonate and 3 parts of sodium lignin sulfonate were uniformly mixed and pulverized to obtain a wettable powder.

FORMULATION EXAMPLE 3

Dust

Two parts of Compound No. 22, 5 parts of diatomaceous earth and 93 parts of clay were uniformly mixed and pulverized to obtain a dust.

FORMULATION EXAMPLE 4

Granule

Five parts of Compound No. 26, 2 parts of sodium lauryl alcohol sulfate, 5 parts of sodium lignin sulfonate, 2 parts of carboxymethylcellulose and 86 parts of clay were uniformly mixed and pulverized. This mixture was kneaded with 20 parts of water, and granulated to a size of from 14 to 32 mesh by an extrusion-type granulator, followed by drying to obtain a granule formulation.

The insecticide of the present invention exhibits excellent insecticidal activities against planthoppers such as brown rice planthopper (*Nilaparvata lugens* Stal), whitebacked rice planthopper. (*Sogatella furcifera* Horvath) and small brown planthopper (*Laodelphax striatellus* Fallen), coleoptera such as rice water weevil (*Lissorhoptrus oryzophilus* Kuschel) and it has extremely high penetration insecticidal activities. Further, it is also effective for the control of Hemiptera such as leaf hoppers, aphids and stink bugs, Lepidoptera such as diamondback moth (*Plutella xylostella* Linne) and common cutworm (*Spodoptera litura* Fabricius), Diptera such as housefly (*Musca domestica* Linne) and mosquito (*Culex pipiens pallens* Coquillett), Coleoptera such as adzuki bean weevil (*Callosobruchus chinensis* Linne), Orthoptera such as German cockroach (*Blattela germanica* Linne) and Mites such as twospotted spider mite (*Tetranychus urticae* Koch) and citrus red mite (*Paronychus citri* McGregor).

Now, the insecticidal activities of the compounds of the present invention will be described with reference to Test Examples. In the following Test Examples, the following compounds were used as Comparative Compounds.

Comparative Compound 1:

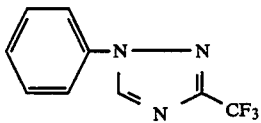

Compound disclosed in U.S. Pat. No. 4,038,405

Comparative Compound 2:

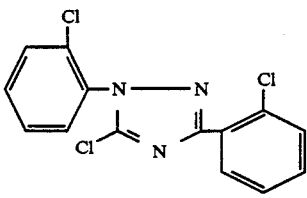

Compound disclosed in Japanese Unexamined Patent Publication No. 19574/1987

TEST EXAMPLE 1

Insecticidal activities against brown rice planthopper

The wettable powder prepared in accordance with Formulation Example 2 was diluted with water to a predetermined concentration. To this insecticidal solution, rice stem and leaf were dipped, and then dried in air and put in a test tube. Ten larvae of brown rice planthopper were put in the test tube, and the test tube was closed with a stopper of absorbent cotton. Then, the test tube was kept in a constant temperature chamber at 25° C. Six days later, the mortality was examined, and the mortality rate was calculated. The test was conducted in two series. The results are shown in Tables 3 to 6.

TABLE 3

| Compound No. | Mortality rate (%) 100 ppm |
|---|---|
| 1 | 100 |
| 2 | 100 |
| 3 | 100 |
| 4 | 100 |
| 5 | 100 |
| 6 | 100 |
| 7 | 100 |
| 8 | 100 |
| 9 | 95 |
| 10 | 95 |
| 11 | 100 |
| 12 | 90 |
| 13 | 100 |
| 14 | 95 |
| 17 | 80 |
| 18 | 100 |
| 19 | 100 |
| 20 | 100 |
| 21 | 100 |
| 22 | 100 |
| 23 | 100 |
| 24 | 100 |
| 25 | 100 |
| 26 | 100 |
| 27 | 95 |
| 28 | 95 |
| 29 | 100 |
| 30 | 95 |
| 31 | 100 |
| 32 | 100 |
| 33 | 100 |
| 34 | 100 |
| 35 | 100 |
| 36 | 100 |
| 37 | 100 |
| 38 | 100 |
| 39 | 100 |
| 40 | 100 |
| 41 | 100 |
| 42 | 100 |
| 43 | 100 |
| 44 | 100 |
| 45 | 100 |
| 46 | 100 |
| 47 | 100 |
| 48 | 100 |
| 49 | 100 |
| 50 | 100 |
| 51 | 100 |
| 52 | 100 |
| 53 | 100 |
| 54 | 100 |
| 55 | 100 |
| 56 | 100 |
| 57 | 100 |
| 58 | 100 |
| 59 | 100 |
| 60 | 100 |
| 61 | 90 |
| 62 | 100 |
| 63 | 100 |
| 64 | 100 |
| 65 | 100 |
| 66 | 100 |
| 67 | 100 |
| 68 | 100 |
| 69 | 100 |
| 70 | 90 |
| 72 | 100 |
| 73 | 100 |
| 74 | 100 |
| 75 | 100 |
| 76 | 100 |
| 79 | 100 |
| 80 | 100 |
| 81 | 100 |
| 82 | 100 |
| 83 | 100 |
| 84 | 100 |
| 85 | 90 |

TABLE 3-continued

| Compound No. | Mortality rate (%) 100 ppm |
|---|---|
| 86 | 100 |

TABLE 4

| Compound No. | Mortality rate (%) 100 ppm | Mortality rate (%) 20 ppm |
|---|---|---|
| 6 | 100 | 100 |
| 8 | 100 | 100 |
| 13 | 100 | 100 |
| 21 | 100 | 100 |
| 22 | 100 | 100 |
| 24 | 100 | 100 |
| 26 | 100 | 100 |
| 28 | 100 | 100 |
| 29 | 100 | 100 |
| 33 | 100 | 100 |
| 34 | 100 | 100 |
| 87 | 100 | 100 |
| 89 | 100 | 80 |
| 90 | 100 | 60 |
| 91 | 100 | 100 |
| 93 | 100 | 100 |
| 94 | 100 | 100 |
| 95 | 100 | 100 |
| 96 | 100 | 100 |
| 97 | 100 | 90 |
| 98 | 100 | 100 |
| 99 | 100 | 85 |
| 100 | 100 | 100 |
| 101 | 100 | 100 |
| 103 | 100 | 80 |
| 104 | 100 | 100 |
| 105 | 100 | 100 |
| 106 | 100 | 100 |
| 107 | 100 | 100 |
| 108 | 100 | 100 |
| 109 | 100 | 90 |
| 110 | 100 | 100 |
| 112 | 100 | 100 |
| 113 | 100 | 100 |
| 114 | 100 | 100 |
| 115 | 100 | 100 |
| Comparative compound 1 | 60 | 40 |
| Comparative compound 2 | 0 | 0 |

TABLE 5

| Compound No. | Mortality rate (%) 100 ppm |
|---|---|
| 116 | 95 |
| 117 | 100 |
| 118 | 100 |
| 119 | 100 |
| 120 | 100 |
| 121 | 100 |
| 122 | 80 |
| 123 | 90 |
| 124 | 100 |
| 125 | 100 |
| 126 | 100 |
| 127 | 100 |
| 128 | 100 |
| 129 | 100 |
| 130 | 100 |
| 131 | 100 |
| 132 | 90 |
| 133 | 100 |
| 134 | 100 |
| 135 | 100 |
| 136 | 100 |
| 137 | 100 |
| 138 | 100 |
| Comparative compound 1 | 65 |
| Comparative compound 2 | 0 |

TABLE 6

| Compound No. | Mortality rate (%) 100 ppm |
|---|---|
| 142 | 75 |
| 143 | 100 |
| 144 | 100 |
| 145 | 70 |
| 148 | 100 |
| 149 | 95 |
| 150 | 100 |
| 151 | 100 |
| 154 | 100 |
| 155 | 100 |
| 156 | 100 |
| 157 | 100 |
| 158 | 100 |
| 159 | 100 |
| 160 | 100 |
| 161 | 100 |
| 162 | 100 |
| 163 | 100 |
| 164 | 100 |
| 165 | 100 |
| 166 | 100 |
| 167 | 100 |
| 168 | 100 |
| 169 | 100 |
| 172 | 100 |
| 173 | 100 |
| 174 | 85 |
| 175 | 100 |
| 177 | 75 |
| 178 | 100 |
| 179 | 100 |
| 180 | 80 |
| 182 | 100 |
| 183 | 100 |
| 184 | 80 |
| 185 | 100 |
| 186 | 100 |
| 187 | 100 |
| 188 | 95 |
| 189 | 90 |
| 190 | 100 |
| 193 | 100 |
| 194 | 100 |
| 197 | 100 |
| 198 | 80 |
| 199 | 100 |
| 200 | 100 |
| 202 | 100 |
| Comparative compound 1 | 65 |
| Comparative compound 2 | 0 |

TEST EXAMPLE 2

Insecticidal activities against rice water weevil

The wettable powder prepared in accordance with Formulation Example 2 was diluted with water to bring the concentration of the active ingredient to a level of 10 ppm. This insecticidal solution was put in a polyethylene cup having a diameter of 9 cm, and ten adults of rice water weevil were put into the cup, and a cover was placed on the cup. Then, the cup was kept in a constant temperature chamber at 25° C. Two days later, the mortality was examined, and the mortality rate was calculated. The test was conducted in two series. The results are shown in Tables 7 and 8.

TABLE 7

| Compound No. | Mortality rate (%) |
| --- | --- |
| 89 | 100 |
| 90 | 90 |
| 91 | 100 |
| 93 | 100 |
| 94 | 100 |
| 95 | 100 |
| 96 | 100 |
| 98 | 100 |
| 100 | 100 |
| 101 | 90 |
| 104 | 100 |
| 105 | 100 |
| 106 | 100 |
| 109 | 100 |
| 111 | 90 |
| 112 | 100 |
| 5 | 100 |
| 8 | 100 |
| 13 | 100 |
| 21 | 100 |
| 22 | 100 |
| 24 | 80 |
| 26 | 100 |
| 28 | 100 |
| 29 | 100 |
| 69 | 100 |
| 70 | 100 |
| 84 | 100 |
| 113 | 100 |
| 114 | 100 |
| 115 | 100 |
| 118 | 100 |
| 124 | 90 |
| 134 | 100 |
| 135 | 80 |
| 136 | 100 |
| Comparative compound 1 | 0 |
| Comparative compound 2 | 0 |

TABLE 8

| Compound No. | Mortality rate (%) |
| --- | --- |
| 138 | 100 |
| 144 | 100 |
| 146 | 100 |
| 151 | 80 |
| 154 | 100 |
| 155 | 100 |
| 156 | 100 |
| 158 | 100 |
| 159 | 100 |
| 160 | 100 |
| 162 | 100 |
| 164 | 100 |
| 167 | 90 |
| 169 | 80 |
| 172 | 100 |
| 173 | 100 |
| 174 | 100 |
| 176 | 100 |
| 178 | 100 |
| 180 | 100 |
| 187 | 90 |
| 190 | 100 |
| 193 | 80 |
| 194 | 100 |
| 196 | 100 |
| 197 | 100 |
| 198 | 100 |
| 199 | 100 |
| 200 | 100 |
| 205 | 80 |
| Comparative compound 1 | 0 |
| Comparative compound 2 | 0 |

TEST EXAMPLE 3

Insecticidal activities against diamondback moth

The wettable powder prepared in the same manner as in Formulation Example 2 was diluted with water to bring the concentration of the active ingredient to a level of 500 ppm. In this insecticidal solution, a leaf of cabbage was immersed, and then it was dried in air and put in a polyethylene cup having a diameter of 5.5 cm. Then, ten larvae of diamondback moth were put in the cup, and a cover was placed on the cup. Then, the cup was kept in a constant temperature chamber at 25° C. Three days later, the mortality was examined, and the mortality rate was calculated. The test was conducted in two series. The results are shown in Tables 9 and 10.

TABLE 9

| Compound No. | Mortality rate (%) |
| --- | --- |
| 21 | 100 |
| 22 | 100 |
| 29 | 95 |
| 34 | 100 |
| 67 | 95 |
| 69 | 100 |
| 89 | 100 |
| 93 | 90 |
| 94 | 100 |
| 95 | 100 |
| 96 | 100 |
| 98 | 75 |
| 100 | 75 |
| 101 | 100 |
| 104 | 100 |
| 105 | 100 |
| 108 | 100 |
| 109 | 95 |
| 112 | 100 |
| 119 | 100 |
| 120 | 75 |
| 121 | 100 |
| 127 | 100 |
| 133 | 75 |

TABLE 10

| Compound No. | Mortality rate (%) |
| --- | --- |
| 134 | 100 |
| 136 | 100 |
| 138 | 100 |
| 152 | 90 |
| 153 | 95 |
| 154 | 85 |
| 155 | 75 |
| 159 | 85 |
| 164 | 100 |
| 166 | 100 |
| 167 | 100 |
| 168 | 100 |
| 169 | 100 |
| 172 | 90 |
| 173 | 100 |
| 184 | 90 |
| 185 | 100 |
| 187 | 100 |
| 188 | 100 |
| 190 | 100 |
| 193 | 100 |
| 194 | 100 |
| 205 | 100 |

TEST EXAMPLE 4

Penetration test against small brown planthopper

The wettable powder prepared in accordance with the Formulation Example 2 was diluted with water to bring the concentration of the active ingredient to a level of 10 ppm. This insecticidal solution is put in a bottle, and the root portion of a rice seedling was dipped therein and fixed with a rubber stopper. A wire gauze cage was put thereon. Ten female adults of small brown planthopper were put therein, and a wire gauze cover was put thereon. Then, the wire gauze cage was kept in a constant temperature chamber at 25° C. Two days later, the mortality was examined and the mortality rate was calculated. The test was conducted in two series. The results are shown in Table 11.

TABLE 11

| Compound No. | Mortality rate (%) |
|---|---|
| 90 | 100 |
| 118 | 100 |
| 119 | 100 |
| 120 | 100 |
| 123 | 100 |
| 135 | 100 |
| 138 | 100 |
| 154 | 100 |
| 156 | 100 |
| 160 | 100 |
| Comparative compound 1 | 0 |
| Comparative compound 2 | 0 |

TEST EXAMPLE 5

Penetration test against small brown planthopper

The wettable powder prepared in accordance with the Formulation Example 2 was diluted with water to bring the concentration of the active ingredient to a level of 2 ppm. This insecticidal solution is put in a bottle, and the root portion of a rice seedling was dipped therein and fixed with a rubber stopper. A wire gauze cage was put thereon. Ten female adults of small brown planthopper were put therein, and a wire gauze cover was put thereon. Then, the wire gauze cage was kept in a constant temperature chamber at 25° C. Two days later, the mortality was examined and the mortality rate was calculated. The test was conducted in two series. The results are shown in Table 12.

TABLE 12

| Compound No. | Mortality rate (%) |
|---|---|
| 90 | 100 |
| 119 | 100 |
| 135 | 100 |
| 154 | 100 |

TEST EXAMPLE 6

Insecticidal activities against small brown planthopper

The wettable powder prepared in accordance with Formulation Example 2 was diluted with water to bring the concentration of the active ingredient to a level of 20 ppm. In this insecticidal solution, the foliage of a rice seedling was dipped for 10 seconds, and the root portion of the rice seedling was dipped in a bottle containing water and fixed with a rubber stopper. After drying the rice seedling in air, a wire gauze cage was put thereon. Ten female adults of small brown planthopper was put therein, and a wire gauze cover was placed thereon. Then, the wire gauze cage was placed in a constant temperature chamber at 25° C. Two days later, the mortality was examined, and the mortality rate was calculated. The test was conducted in two series. The results are shown in Table 13.

TABLE 13

| Compound No. | Mortality rate (%) |
|---|---|
| 80 | 100 |
| 87 | 100 |
| 96 | 100 |
| 98 | 100 |
| 104 | 100 |
| 114 | 100 |
| 127 | 100 |
| Comparative compound 1 | 10 |
| Comparative compound 2 | 0 |

TEST EXAMPLE 7

Insecticidal activities against small brown planthopper

The wettable powder prepared in accordance with Formulation Example 2 was diluted with water to bring the concentration of the active ingredient to a level of 4 ppm. In this insecticidal solution, the foliage of a rice seedling was dipped for 10 seconds, and the root portion of the rice seedling was dipped in a bottle containing water and fixed with a rubber stopper. After drying the rice seedling in air, a wire gauze cage was put thereon. Ten female adults of small brown planthopper was put therein, and a wire gauze cover was placed thereon. Then, the wire gauze cage was placed in a constant temperature chamber at 25° C. Two days later, the mortality was examined, and the mortality rate was calculated. The test was conducted in two series. The results are shown in Table 14.

TABLE 14

| Compound No. | Mortality rate (%) |
|---|---|
| 87 | 100 |
| 96 | 100 |
| 104 | 100 |
| 127 | 100 |

We claim:

1. A phenyltriazole derivative of the formula:

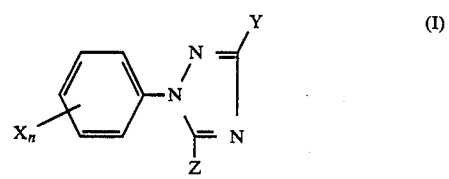

wherein X is a halogen atom, an alkyl group, a halogen-substituted alkyl group, an alkoxy group, a nitro group, a phenoxy group, an amino group, a cyano group, a 1-pyrrolyl group or a halogen-substituted alkoxy group, Y is a $C_2$-$C_6$ alkyl group which may be substituted by halogen, alkoxy, alkyl thio, alkylsulfonyl, alkoxycarbonyl or carbamoyl, a methyl-substituted cycloalkyl group, an alkenyl group, a $C_1$-$C_4$ alkylsulfinyl group or a 2-methyl-1,3-dithiolan-2-yl group, Z is, a

group, wherein each of $R^1$ and $R^2$ which may be the same or different is a hydrogen atom, an alkyl group, an alkoxy group, an acyl group, an amino group, a phenyl group, an alkenyl group, an alkynyl group, a dimethylcarbamoyl group, an alkoxycarbonyl group, a trichloromethylthio group or an alkylsulfonyl group which may be substituted by halogen, or $R^1$ and $R^2$ form together with the adjacent nitrogen atom, a pyrrole or a pyrazole ring, and n is an integer of 0 to 5.

2. The phenyltriazole derivative according to claim 1, which has the formula:

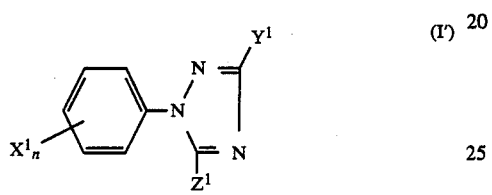
(I')

wherein $X^1$ is a halogen atom, a trifluoromethyl group, a trifluoromethoxy group, a nitro group or a 1-pyrrolyl group, $Y^1$ is a $C_2$–$C_6$ alkyl group which may be substituted by halogen, a methylsulfinyl group or a

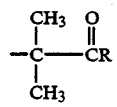

group wherein R is an alkoxy group or an amino group, $Z^1$ is a 1-pyrrolyl group or a

group wherein each of $R^{3'}$ and $R^{4'}$ which may be the same or different is a hydrogen atom, an acyl group, an alkenyl group, an alkynyl group, an alkyl group, an alkoxy group, a trichloromethylthio group, a dimethylcarbamoyl group, a methanesulfonyl group which may be substituted by chlorine, or an alkoxycarbonyl group, and n is 2 or 3.

3. The phenyltriazole derivative according to claim 1, which has the formula:

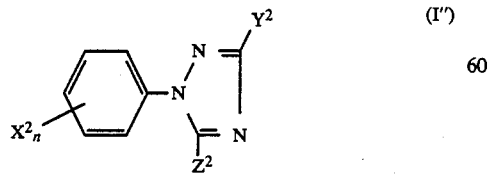
(I'')

wherein $X^2$ is a halogen atom, a trifluoromethyl group, a trifluoromethoxy group or a nitro group, $Y^2$ is a $C_2$–$C_4$ alkyl group, $Z^2$ is a 1-pyrrolyl group of a

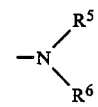

group wherein each of $R^5$ and $R^6$ which may be the same or different is a hydrogen atom, an alkyl group, an alkynyl group, an alkoxy groups, an acyl group, an alkenyl group, an alkoxycarbonyl group or a trichloromethylthio group, and n is an integer of from 0 to 5.

4. The phenyltriazole derivative according to claim 1, which has the formula:

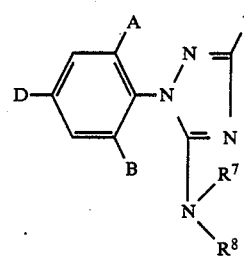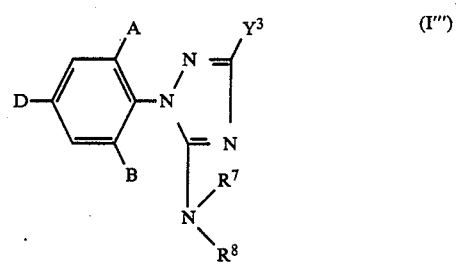
(I''')

wherein each of A and B which may be the same or different is a chlorine atom or a nitro group, D is a trifluoromethyl group or a trifluoromethoxy group, $Y^3$ is a $C_2$–$C_4$ alkyl group which may be substituted by halogen, and each of $R^7$ and $R^8$ which may be the same or different is a hydrogen atom, an acyl group, an alkenyl group, an alkynyl group or an alkyl group.

5. The phenyltriazole derivative according to claim 4, wherein $Y^3$ is a butyl group or a $C_2$–$C_4$ alkyl group which is substituted by halogen.

6. The phenyltriazole derivative according to claim 1, which has the formula:

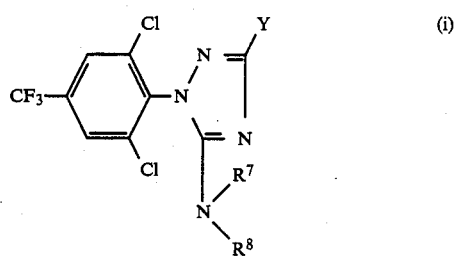
(i)

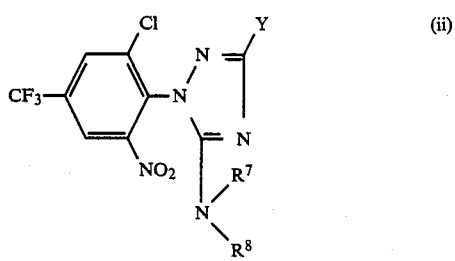
(ii)

-continued

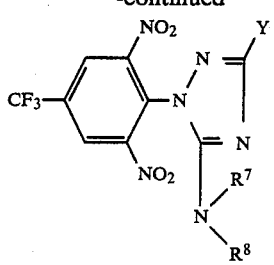
(iii)

or

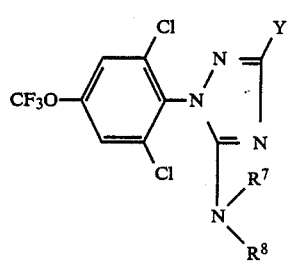
(iv)

wherein Y is as defined in claim 1, and each of $R^7$ and $R^8$ which may be the same or different is a hydrogen atom, an acyl group, an alkenyl group, an alkynyl group or an alkyl group.

7. The phenyltriazole derivative according to claim 6, wherein Y is a tertiary butyl group.

8. The phenyltriazole derivative according to claim 6, wherein Y is a $C_2$–$C_4$ alkyl group which is substituted by halogen.

9. The phenyltriazole derivative according to claim 6, wherein each of $R^7$ and $R^8$ which may be the same or different is a hydrogen atom, a methyl group, an ethyl group or a propyl group.

10. An insecticide comprising an insecticidally effective amount of a phenyltriazole derivative of the formula I as defined in claim 1 and an agricultural carrier.

11. The phenyltriazole derivative according to claim 1, which has the formula:

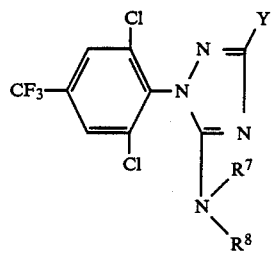
(i)

wherein Y is as defined in claim 1, and each of $R^7$ and $R^8$ which may be the same or different is a hydrogen atom, an acyl group, an alkenyl group, an alkynyl group or an alkyl group.

12. The phenyltriazole derivative according to claim 1, which has the formula:

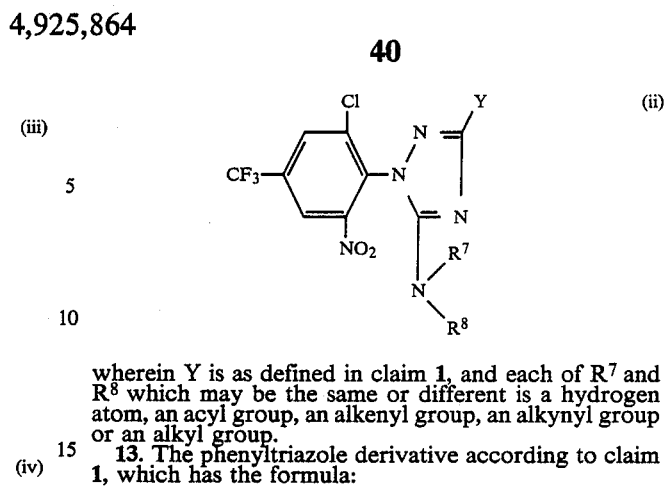

wherein Y is as defined in claim 1, and each of $R^7$ and $R^8$ which may be the same or different is a hydrogen atom, an acyl group, an alkenyl group, an alkynyl group or an alkyl group.

13. The phenyltriazole derivative according to claim 1, which has the formula:

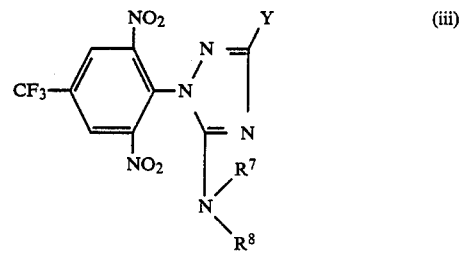
(iii)

wherein Y is as defined in claim 1, and each of $R^7$ and $R^8$ which may be the same or different is a hydrogen atom, an acyl group, an alkenyl group, an alkynyl group or an alkyl group.

14. The phenyltriazole derivative according to claim 1, which has the formula:

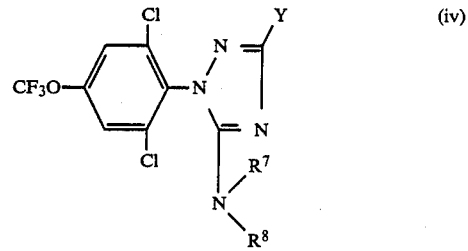
(iv)

wherein Y is as defined in claim 1, and each of $R^7$ and $R^8$ which may be the same or different is a hydrogen atom, an acyl group, an alkenyl group, an alkynyl group or an alkyl group.

15. The phenyltriazole derivative according to claim 1, 5-Amino-1-(2,6-dichloro-4-trifluoromethylphenyl)-3-(1,1-dimethylethyl)-1H-1,2,4-triazole.

16. The phenyltriazole derivative according to claim 1, 1-(2,6-dichloro-4-trifluoromethylphenyl)-3-(1,1-dimethylethyl)-5-(N-ethylamino)-1H-1,2,4-triazole.

17. The phenyltriazole derivative according to claim 1, 1-(2,6-dichloro-4-trifluoromethylphenyl)-3-(1,1-dimethylethyl)-5-(N-propylamino)-1H-1,2,4-triazole.

18. The phenyltriazole derivative according to claim 1, 1-(2,6-dichloro-4-trifluoromethylphenyl)-5-(N,N-diethylamino)-3-(1-trifluoromethylethyl)-1H-1,2,4-triazole.

19. The phenyltriazole derivative according to claim 1, 5-amino-1-(2,6-dichloro-4-trifluoromethylphenyl)-3-pentafluoroethyl-1H-1,2,4-triazole.

20. The phenyltriazole derivative according to claim 1, 5-(N,N-diethylamino)-3-(1,1-dimethylethyl)-1-(2,6-dinitro-4-trifluoromethylphenyl)-1H,1,2,4-triazole.

21. The phenyltriazole derivative according to claim 1, 1-(2-chloro-6-nitro-4-trifluoromethylphenyl-5-(N,N-diethylamino)-3-(1,1-dimethylethyl)-1H-1,2,4-triazole.

22. The phenyltriazole according to claim 1, 1-(2,6-dichloro-4-trifluoromethoxyphenyl)-5-(N,N-diethylamino)-3-(1,1-dimethylethyl-1H-1,2,4-triazole.

23. The phenyltriazole according to claim 1, 5-amino-1-(2,4,6-trichloro)-3-tert-butyl-1H-1,2,4-triazole.

* * * * *